(12) United States Patent
Ishikawa

(10) Patent No.: US 7,336,815 B2
(45) Date of Patent: *Feb. 26, 2008

(54) IMAGE DEFECT INSPECTION METHOD, IMAGE DEFECT INSPECTION APPARATUS, AND APPEARANCE INSPECTION APPARATUS

(75) Inventor: Akio Ishikawa, Hachioji (JP)

(73) Assignee: Tokyo Seimitsu Co., Ltd., Tokyo (JP)

( * ) Notice: Subject to any disclaimer, the term of this patent is extended or adjusted under 35 U.S.C. 154(b) by 282 days.

This patent is subject to a terminal disclaimer.

(21) Appl. No.: 11/255,136

(22) Filed: Oct. 19, 2005

(65) Prior Publication Data

US 2006/0126914 A1 Jun. 15, 2006

(30) Foreign Application Priority Data

Dec. 13, 2004 (JP) ............................. 2004-359343
Mar. 30, 2005 (JP) ............................. 2005-098581

(51) Int. Cl.
*G06K 9/00* (2006.01)
(52) U.S. Cl. ...................... 382/145; 382/149; 382/168; 382/169; 382/172
(58) Field of Classification Search ................ 382/149, 382/168, 169, 172
See application file for complete search history.

(56) References Cited

U.S. PATENT DOCUMENTS 4,868,651 A * 9/1989 Chou et al. ................. 378/98.7

(Continued)

FOREIGN PATENT DOCUMENTS

JP 4-107946 4/1992

(Continued)

OTHER PUBLICATIONS

Patent Abstract of Japan, Publication No. 04107946 A, Published on Apr. 9, 1992, in the name of Taniguchi et al.

(Continued)

*Primary Examiner*—Bhavesh M. Mehta
*Assistant Examiner*—John B Strege
(74) *Attorney, Agent, or Firm*—Christie, Parker & Hale, LLP

(57) ABSTRACT

In an image defect inspection method and apparatus which detects a gray level difference between corresponding portions of two images, automatically sets a threshold value based on the distribution thereof, compares the gray level difference with the threshold value, and judges one or the other of the portions to be defective if the gray level difference is larger than the threshold value, provisions are made to enhance defect detection sensitivity by correcting the threshold value when the distribution of the gray level difference is different from the usual distribution. A cumulative frequency of the gray level difference between the corresponding portions of the two images is computed (S103); a converted cumulative frequency is computed by converting the cumulative frequency so that the cumulative frequency shows a linear relationship to the gray level difference when a prescribed distribution is assumed (S104); an approximate straight line is computed in each of two regions, one where the gray level difference is positive and the other where the gray level difference is negative (S105); when the difference between the slopes of the approximate straight lines is larger than a predetermined value (S106), the approximate straight line having the smaller slope is corrected in such a manner the slope increases (S107); and based on the approximate straight line, the threshold value is determined from a prescribed cumulative frequency value in accordance with a prescribed calculation method.

19 Claims, 17 Drawing Sheets

U.S. PATENT DOCUMENTS

| | | | |
|---|---|---|---|
| 6,137,541 A * | 10/2000 | Murayama | 348/673 |
| 6,993,183 B2 * | 1/2006 | Inoue | 382/170 |
| 2004/0062432 A1 | 4/2004 | Ishikawa | |
| 2005/0013475 A1 * | 1/2005 | Levin et al. | 382/145 |

FOREIGN PATENT DOCUMENTS

| | | |
|---|---|---|
| JP | 2996263 | 10/1999 |
| JP | 2002-22421 | 1/2002 |
| JP | 2004-177397 | 6/2004 |

OTHER PUBLICATIONS

Patent Abstract of Japan, Publication No. 05047886 A, Published on Feb. 26, 1993, in the name of Jingu.

Patent Abstract of Japan, Publication No. 2002022421 A, Published on Jan. 23, 2002, in the name of Hikita et al.

Patent Abstract of Japan, Publication No. 2004177397 A, Published on Jun. 24, 2004, in the name of Ishikawa.

* cited by examiner

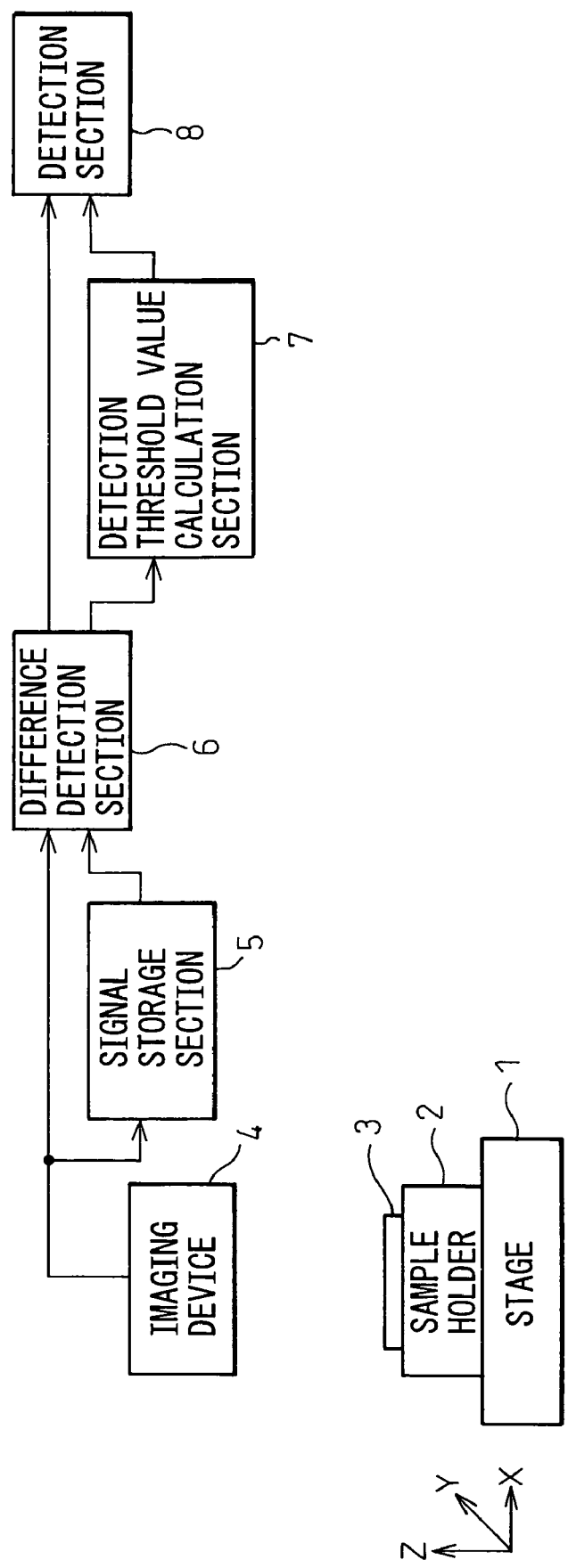

IMAGE DEFECT INSPECTION METHOD, IMAGE DEFECT INSPECTION APPARATUS, AND APPEARANCE INSPECTION APPARATUS

CROSS-REFERENCE TO RELATED APPLICATION

This application claims priority of Japanese Patent Application Number 2004-359343, filed on Dec. 13, 2004, and Japanese Patent Application Number 2005-098581, filed on Mar. 30, 2005.

BACKGROUND OF THE INVENTION

1. Field of the Invention

The present invention relates to a defect inspection method and apparatus which detects a difference between corresponding signals, compares the detected difference with a threshold value, and judges the part under examination to be defective if the difference is larger than the threshold value. More particularly, the invention relates to an image defect inspection method and apparatus which detects a gray level difference between corresponding portions of two images, compares the detected gray level difference with a threshold value, and judges one or the other of the portions to be defective if the gray level difference is larger than the threshold value, and also relates to an appearance inspection apparatus which, by using such a method, detects a defect in a semiconductor circuit pattern formed on a semiconductor wafer. Still more particularly, the present invention relates to a technique for determining such a threshold value in accordance with the above signals (images).

2. Description of the Related Art

The present invention is directed to an image processing method and apparatus which compares corresponding portions in two images that should be the same, and judges any portion where the difference is large to be defective. The description herein is given by taking as an example an appearance inspection apparatus (inspection machine) for detecting a defect in a semiconductor circuit pattern formed on a semiconductor wafer during a semiconductor manufacturing process, but the invention is not limited to this particular type of apparatus. Generally, a bright field inspection apparatus, in which the surface of a sample is illuminated from a vertical direction and the image of its reflected light is captured, is employed for such an appearance inspection apparatus, but a dark field inspection apparatus which does not directly capture the illumination light is also used. In the case of the dark field inspection apparatus, the surface of the sample is illuminated from an oblique or a vertical direction, and a sensor is disposed so as not to detect specularly reflected light. Then, the dark field image of the surface of the sample is obtained by sequentially scanning the surface with the illumination light. Accordingly, some dark field apparatuses may not use an image sensor, but it will be appreciated the present invention is also applicable to such apparatuses. In this way, the present invention is applicable to any image processing method and apparatus as long as the method and apparatus are designed to compare corresponding portions between two images (signals) that should be the same, and to judge any portion where the difference is large to be defective.

In the semiconductor manufacturing process, many chips (dies) are formed on a semiconductor wafer. Patterns are formed in multiple layers on each die. Each completed die is electrically tested using a prober and a tester, and any defective die is removed from the assembly process. In the semiconductor manufacturing process, manufacturing yield is a very important factor, and the result of the electrical testing is fed back to the manufacturing process and used for the management of each process step. However, as the semiconductor manufacturing process consists of many process steps, it takes a very long time before the electrical testing can be conducted after the manufacturing is started. Therefore, when, for example, a certain process step is found to be faulty as a result of the electrical testing, many wafers are already partway through the process and, thus, the result of the electrical testing cannot be easily utilized for improving the yield. In view of this, pattern defect inspection is performed to inspect formed patterns in the middle of the process in order to detect any pattern defects. If the pattern defect inspection is performed at a plurality of steps in the manufacturing process, it becomes possible to detect any defects that occurred after the preceding inspection, and the result of the inspection can thus be promptly reflected in the process management.

In an appearance inspection apparatus currently in use, a semiconductor wafer is illuminated, an image of a semiconductor circuit pattern is optically captured, and an electrical image signal is generated which is further converted into a multi-valued digital signal (digital gray level signal). Then, a difference signal (gray level difference signal) is generated that represents the difference between the gray level signal of the pattern under inspection and the gray level signal of a reference pattern, and any portion where the difference is larger than a predetermined threshold value is judged to be defective.

Generally, the reference pattern is a neighboring die or a neighboring similar pattern. Then, a defect grouping process is performed in which the portion that has been judged to be defective is examined in further detail to determine whether the defect is a true defect that affects the yield. The defect grouping process takes a long processing time because each defective portion needs to be examined in detail. Therefore, in the defect judgment, it is required that any true defect be invariably judged to be a defect, while minimizing the possibility of judging any defect other than a true defect to be a defect.

To achieve this, optimum setting of the threshold value is critical. If the threshold value is set too small, the number of pixels judged to be defective will increase, and portions not truly defective will be judged defective, thus resulting in the problem that the time required for the defect grouping process increases. Conversely, if the threshold value is set too large, even true defects may be judged not to be defects, resulting in the problem that the inspection is inadequate.

In a prior art method that automatically determines the threshold value according to each sample, the digital gray level signal of the pattern of a similar sample is generated in advance, followed by the generation of a gray level difference signal, and a histogram of gray level differences is created. Then, a variation reference difference, which is set by a prescribed proportion of a portion where the gray level difference is large in the histogram, is obtained, and the threshold value for detection is determined by adding a fixed difference to the reference difference. The reason for this is to prevent the number of pixels judged to be defective from increasing appreciably in cases where the variance of the distribution of the differences is large, by considering that such cases can become a problem in practice. In this method, the variation reference difference varies from sample to sample, but the fixed difference to be added is fixed and does not vary from sample to sample; accordingly, this method has the problem that the proper threshold value cannot be determined when the noise level varies.

To solve the above problem, various methods for determining the threshold value have been proposed. For example, Japanese Unexamined Patent Publication No. H04-107946 discloses a method that determines the threshold value based on the statistics of gray level differences computed at a plurality of portions of a pattern. More specifically, a histogram of maximum values is created by obtaining the maximum value of the gray level difference for each portion. Then, based on the mean and standard deviation of the gray level difference, the initial value of the optimum threshold value is set, and the optimum threshold value is determined by correcting the initial value based on the number of pixels detected as defective. This method, however, has the following problems: (1) samples must be measured in advance and (2) inspection must be performed a plurality of times. Furthermore, while it is stated that the threshold value at which the number of detected defects suddenly changes is optimum, no description is provided of a specific method for obtaining such a threshold value.

On the other hand, Japanese Patent No. 2996263 discloses a method in which an approximate curve is obtained from the relationship between the gray level difference and its frequency and the gray level difference at which the approximate curve becomes zero is taken as the optimum threshold value. Here, the relationship between the gray level difference and the frequency is represented by a curve, but a curve does not necessarily become zero; therefore, there are cases where the approximate curve does not become zero. Further, even in the case of a straight line, the straight line may not become zero, depending on its slope. Therefore, there can occur cases where the threshold value cannot be set. Furthermore, it is stated that the above curve can be obtained easily, but in actuality, this curve cannot be obtained easily because it depends on the distribution of gray level differences, and hence there arises the problem that the processing time increases.

Japanese Unexamined Patent Publication No. 2002-22421 discloses a method that performs a conversion to an error probability value by using a standard deviation. This method, however, involves the following problems: (1) as the standard deviation is computed directly from the gray level differences, a large amount of computation is required and the processing time increases, and (2) as the error probability value, and not the gray level difference, is used to judge the presence or absence of a defect, the error probability value must be computed for every gray level difference, and this again increases the processing time. There is the further problem that, because of the use of the standard deviation, the method is only applicable to normal distributions and cannot be applied to other types of distribution.

For the inspection of semiconductor patterns, etc., it is desired to automate the inspection process, and it is also desired to automatically set the threshold value. To achieve this, there is a need to set the optimum threshold value by instantaneously processing the detected gray level differences and to judge the presence or absence of a defect based on the threshold value; one possible solution here would be to automatically set the threshold value by automatically performing a method such as described above. On the other hand, there is also a need to shorten the inspection time in order to improve throughput, but the above-described methods have problems such as the need to measure the samples a plurality of times in advance, the long processing time, etc. and therefore, are not suitable for automating the threshold value setting process in a high-throughout inspection apparatus.

In particular, in the inspection of an actual semiconductor pattern, the noise level differs depending not only on the portion within a die but also on the position of the die on the wafer; furthermore, even when the same semiconductor pattern is formed, the noise level differs from one wafer to another. Accordingly, there is a need to set the optimum threshold value by processing the gray level difference as it is detected, but none of the above-described prior art methods can satisfy such a need.

In view of the above background, the applicant of this patent application proposed the following image defect inspection method in Japanese Unexamined Patent Publication No. 2004-177397. That is, the distribution (histogram) of the gray level difference between corresponding portions of two images is created (see FIG. 1A), and its cumulative frequency is computed (see FIG. 1B). Then, assuming that the gray level difference has a distribution that obeys a prescribed type of distribution, a converted cumulative frequency is computed by converting the cumulative frequency so that the cumulative frequency show a linear relationship to the gray level difference (see FIG. 1C). After that, an approximate straight line is computed by approximating the converted cumulative frequency by a straight line and, based on the computed approximate straight line, the threshold value is determined from a prescribed cumulative frequency value in accordance with a prescribed calculation method.

For example, in the example of FIG. 1C, the threshold value T is calculated as $T=(P1-b+VOP)/a+HO$, where "a" is the slope of the approximate straight line, "b" is the intercept at which the approximate straight line intersects the vertical axis, P1 is the cumulative frequency corresponding to the prescribed cumulative probability (p), and VOP and HO are prescribed sensitivity setting parameters.

As the converted cumulative frequency computed with this method shows a linear relationship with the gray level difference, subsequent processing for determining the threshold value is facilitated; as a result, the threshold value can be set automatically in a short processing time.

SUMMARY OF THE INVENTION

However, in the method that determines the detection threshold value based on the distribution of the detected gray level difference signal as disclosed in the above cited Japanese Unexamined Patent Publication No. 2004-177397, if the actual distribution of the gray level difference of the image under inspection is different from the prescribed type of distribution assumed when computing the converted cumulative frequency, there arises the problem that the approximate straight line of the converted cumulative frequency is adversely affected, resulting in an incorrect setting of the detection threshold value.

If, for example, the image under inspection contains a giant defect (i.e., a defect that cannot be disregarded in relation to the population of the pixels of the image under inspection) which manifests itself as a portion "r" in a region where the gray level difference is large, as shown in FIG. 2A, and cumulative frequency is computed from this histogram, the graph shown in FIG. 2B will result. Here, dashed line A indicates the graph that would result if there were no such defect, while semi-dashed line B shows the graph in the presence of the defect. If these cumulative frequencies are converted to produce converted cumulative frequencies, the dashed line C in FIG. 2C and the dashed line E in FIG. 2D will be respectively obtained.

As shown, the dashed line C, in the absence of the giant defect, is well approximately by a straight line; on the other hand, in the case of the dashed line E, in the presence of the giant defect, the converted cumulative frequency is approximated by a straight line up to the point of a certain gray level difference but, in the larger gray level difference region beyond that point, the straight line is shifted in a step-like manner, resulting in a discontinuous graph.

Accordingly, in the case of FIG. 2C, that is, when there is no giant defect, the approximate straight line of the converted cumulative frequency will be obtained as shown by a solid line D while, in the case of FIG. 2D, that is, when there is a giant defect in the positive gray level difference region, the approximate straight lines in the positive and negative gray level difference regions will be obtained as shown by solid lines F and G, respectively. That is, when there is a giant defect, the slope of the approximate straight line in the positive gray level difference region, as indicated by the solid line G, is smaller than that of the approximate straight line indicated by the solid line D and, as a result, the threshold value is set larger and the detection sensitivity drops.

In view of the above problem, it is an object of the present invention to provide an image defect inspection method and apparatus which detects a gray level difference between corresponding portions of two images, automatically sets a threshold value based on the distribution of the detected gray level difference, compares the detected gray level difference with the threshold value, and judges one or the other of the portions to be defective if the gray level difference is larger than the threshold value, wherein provisions are made to be able to perform the defect inspection by maintaining high detection sensitivity while suppressing the occurrence of false defects by correcting the automatically set threshold value when the distribution of the gray level difference of the image under inspection is different from the usual distribution.

To achieve the above object, in the image defect inspection method and the image defect inspection apparatus according to the present invention, a cumulative frequency of the gray level difference between the corresponding portions of the two images is computed; a converted cumulative frequency is computed by converting the cumulative frequency so that the cumulative frequency shows a linear relationship to the gray level difference when the gray level difference is assumed to have a distribution that obeys a prescribed type of distribution; an approximate straight line of the converted cumulative frequency is computed in each of two regions, one where the gray level difference is positive and the other where the gray level difference is negative; when the difference between the slopes of the approximate straight lines is larger than a predetermined value, the approximate straight line having the smaller slope is corrected in such a manner the slope increases; and based on the approximate straight line, the threshold value is determined from a prescribed cumulative frequency value in accordance with a prescribed calculation method.

To correct the approximate straight line having the smaller slope in such a manner the slope increases when the difference between the slopes of the approximate straight lines is larger than the predetermined value, the correction may be made in such a manner the slope increases by a predetermined amount, or in such a manner the slope becomes equal to the slope of the other approximate straight line, or in such a manner the slope becomes equal to an average taken between the slopes of the approximate straight lines.

In an alternative mode of the image defect inspection method and the image defect inspection apparatus according to the present invention, a cumulative frequency of the gray level difference between the two images is computed; a converted cumulative frequency is computed by converting the cumulative frequency so that the cumulative frequency shows a linear relationship to the gray level difference when the gray level difference is assumed to have a distribution that obeys a prescribed type of distribution; an approximate straight line is computed by approximating the converted cumulative frequency by a straight line; a correlation coefficient between the converted cumulative frequency and the gray level difference is computed; based on the approximate straight line, the threshold value is determined from a prescribed cumulative frequency value in accordance with a prescribed calculation method; and the determined threshold value is corrected in accordance with the computed correlation coefficient.

Here, to correct the threshold value, first the prescribed type of distribution is determined by assuming the distribution that the gray level difference will normally exhibit, and then the above determined threshold value is corrected in such a manner the threshold value increases as the computed correlation coefficient decreases; alternatively, the prescribed type of distribution may be determined by assuming the distribution that the gray level difference between two images containing a prescribed amount of noise will exhibit, and the determined threshold value may be corrected in such a manner the threshold value increases as the computed correlation coefficient increases.

In a further alternative mode of the image defect inspection method and the image defect inspection apparatus according to the present invention, a cumulative frequency of the gray level difference between the corresponding portions of the two images is computed; a converted cumulative frequency is computed by converting the cumulative frequency so that the cumulative frequency shows a linear relationship to the gray level difference when the gray level difference is assumed to have a distribution that obeys a prescribed type of distribution; an approximate straight line of the converted cumulative frequency is computed in each of two regions, one where the gray level difference is positive and the other where the gray level difference is negative; at least one of the approximate straight lines is corrected in accordance with the difference between the slopes of the approximate straight lines; and based on the approximate straight line, the threshold value is determined from a prescribed cumulative frequency value in accordance with a prescribed calculation method.

The distribution used here can be any type of distribution; for example, the distribution is one selected from the group consisting of a normal distribution, a Poisson distribution, a t-distribution, an exponential distribution, a Weibull distribution, and a chi-squared distribution.

BRIEF DESCRIPTION OF THE DRAWINGS

These and other objects and features of the present invention will become clearer from the following description of the preferred embodiments given with reference to the attached drawings, wherein:

FIG. 3 is a block diagram showing the general configuration of an appearance inspection apparatus according to a first embodiment of the present invention;

DESCRIPTION OF THE PREFERRED EMBODIMENTS

Preferred embodiments of the present invention will be described in detail below while referring to the attached drawings.

FIG. 3 is a block diagram showing the general configuration of a semiconductor pattern appearance inspection apparatus according to a first embodiment of the present invention. As shown, a sample holder (chuck stage) 2 is mounted on the upper surface of a stage 1 which is freely movable in two or three directions. A semiconductor wafer 3 to be inspected is placed and fixed onto the sample holder. An imaging device 4 comprising a one-dimensional or a two-dimensional CCD camera or the like is disposed above the stage, and the imaging device 4 produces an image signal by capturing an image of a pattern formed on the semiconductor wafer 3.

Figure 4:
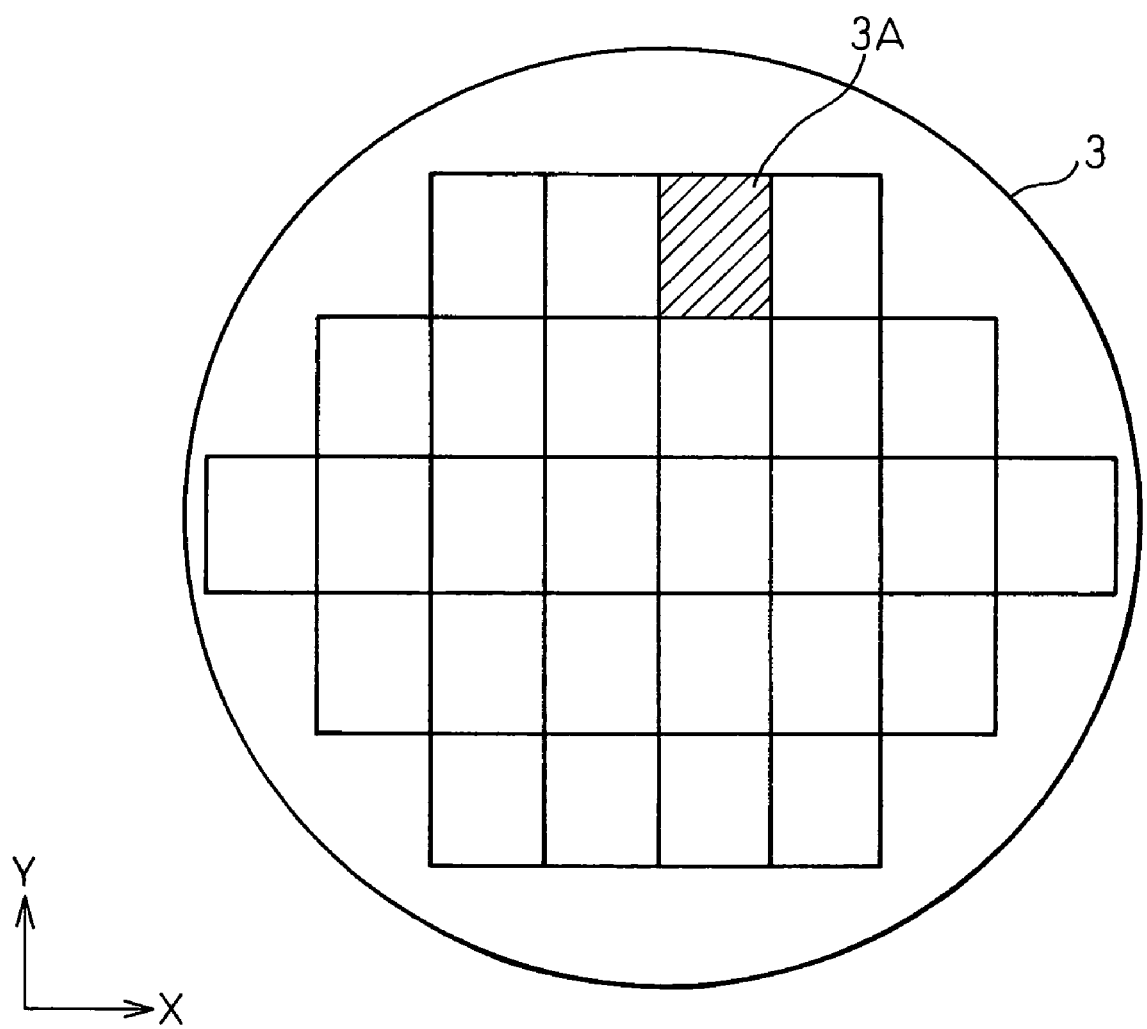
FIG. 4 is a diagram showing an arrangement of dies on a semiconductor wafer.

As shown in FIG. 4, a plurality of dies 3A are formed on the semiconductor wafer 3 in a matrix pattern repeating in X and Y directions. As the same pattern is formed on each die, it is general practice to compare the images of corresponding portions between adjacent dies. If there is no defect in any of the two adjacent dies, the gray level difference between them is smaller than a threshold value, but if there is a defect in either one of the dies, the gray level difference is larger than the threshold value (single detection). At this stage, however, this is no knowing which die contains the defect; therefore, the die is further compared with another die adjacent on a different side and, if the gray level difference in the same portion is larger than the threshold value, then it is determined that the die is defective (double detection).

The imaging device 4 is constructed from a one-dimensional CCD camera, and the stage 1 moves so that the imaging device 4 moves (scans) at a constant speed in the X or Y direction relative to the semiconductor wafer 3. The image signal is converted into a multi-valued digital signal (gray level signal) which is supplied to a difference detection section 6 and also to a signal storage section 5 for storing therein. As the scanning proceeds, a gray level signal is generated from the adjacent die, in synchronism with which the gray level signal of the preceding die is read out of the signal storage section 5 and supplied to the difference detection section 6. Actually, processing such as fine registration is also performed, but a detailed description of such processing will not be given here.

In this way, the gray level signals of the two adjacent dies are input to the difference detection section 6 where the difference (gray level difference) between the two gray level signals is computed, which is then supplied to a detection threshold value calculation section 7 and a detection section 8. Here, the difference detection section 6 computes the gray level difference (with a positive or negative sign) and outputs it as the gray level difference. The detection threshold value calculation section 7 determines the detection threshold value based on the gray level difference and supplies it to the detection section 8. The detection section 8 compares the gray level difference with the thus determined threshold value to determine whether a defect exists. Generally, the noise level of a semiconductor pattern differs depending on the kind of the pattern such as the pattern of a memory cell portion, the pattern of a logic circuit portion, the pattern of a wiring portion, or the pattern of an analog circuit portion. Correspondence between each portion and the kind of the semiconductor pattern can be found from the design data. Therefore, for example, the detection threshold value calculation section 7 determines the threshold value by performing threshold value determining processing for each portion, and the detection section 8 makes a decision by using the threshold value determined for each portion.

In the present embodiment, the signal storage section 5 is provided in order to compare the images of adjacent dies on the semiconductor wafer, but the gray level difference can also be generated by supplying to the difference detection section 6 the image signal of a reference sample separately stored or an image signal generated from data such as CAD; in that case, the signal storage section 5 can be eliminated.

The general configuration of the appearance inspection apparatus of the first embodiment has been described above, but the feature of the present invention lies in the provision of the detection threshold value calculation section 7, the general configuration of which will be described with reference to the block diagram of FIG. 5.

Figure 5:
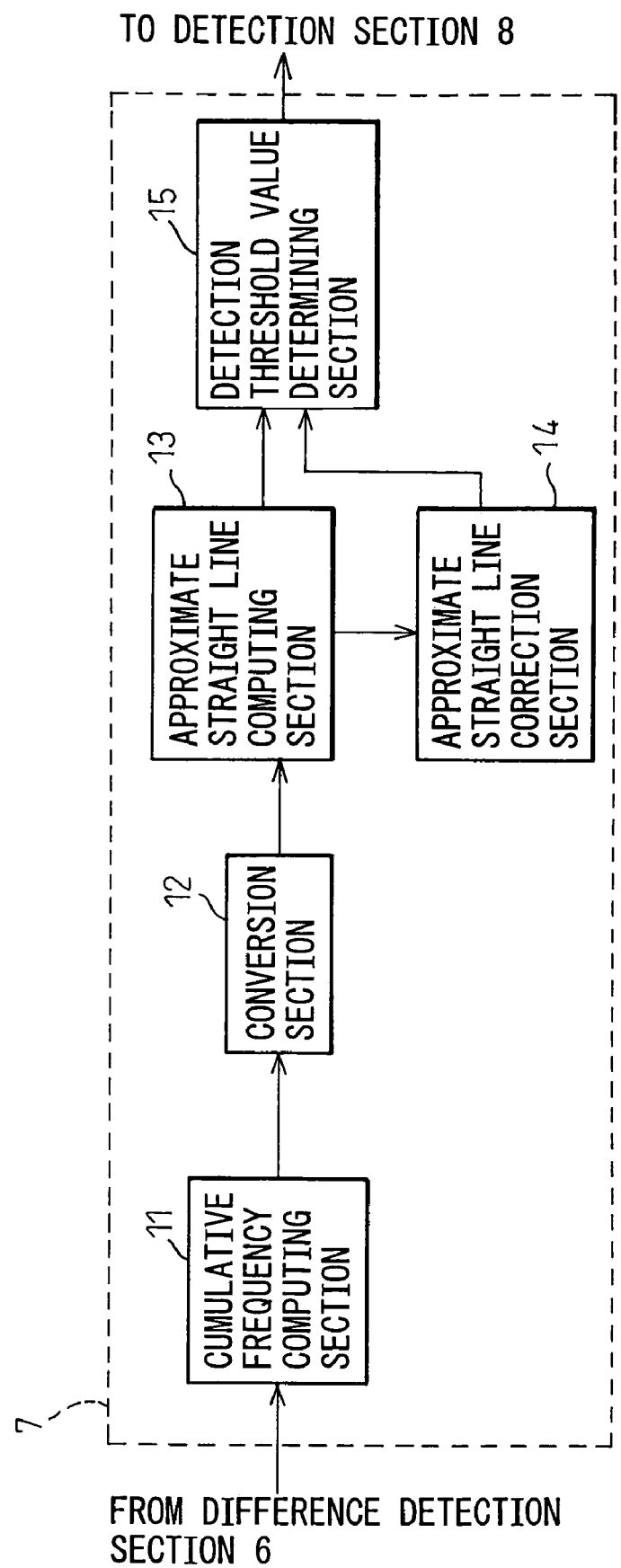
FIG. 5 is a block diagram showing the general configuration of a detection threshold value calculation section in the appearance inspection apparatus of FIG. 3.

FIG. 5 is a block diagram showing the general configuration of the detection threshold value calculation section 7.

As shown, the detection threshold value calculation section 7 comprises: a cumulative frequency computing section 11 which takes as an input the positive- or negative-signed gray level difference supplied from the difference detection section 6, and computes its cumulative frequency; a conversion section 12 which takes the cumulative frequency as an input, and computes a converted cumulative frequency by converting the cumulative frequency so that the cumulative frequency shows a linear relationship to the gray level difference; an approximate straight line computing section 13 which approximates the converted cumulative frequency by a straight line in each of the positive and negative gray level difference regions, and computes approximate straight lines in the respective regions; an approximate straight line correction section 14 which, when the difference between the slopes of the approximate straight lines is larger than a predetermined value, corrects the approximate straight line having the smaller slope; and a threshold value determining section 15 which, based on the approximate straight line, determines the threshold value from a prescribed cumulative frequency value in accordance with a prescribed calculation method.

The operation of the thus configured detection threshold value calculation section 7 and its component elements will be described with reference to FIG. 1 and FIGS. 6 to 10.

Figure 6:
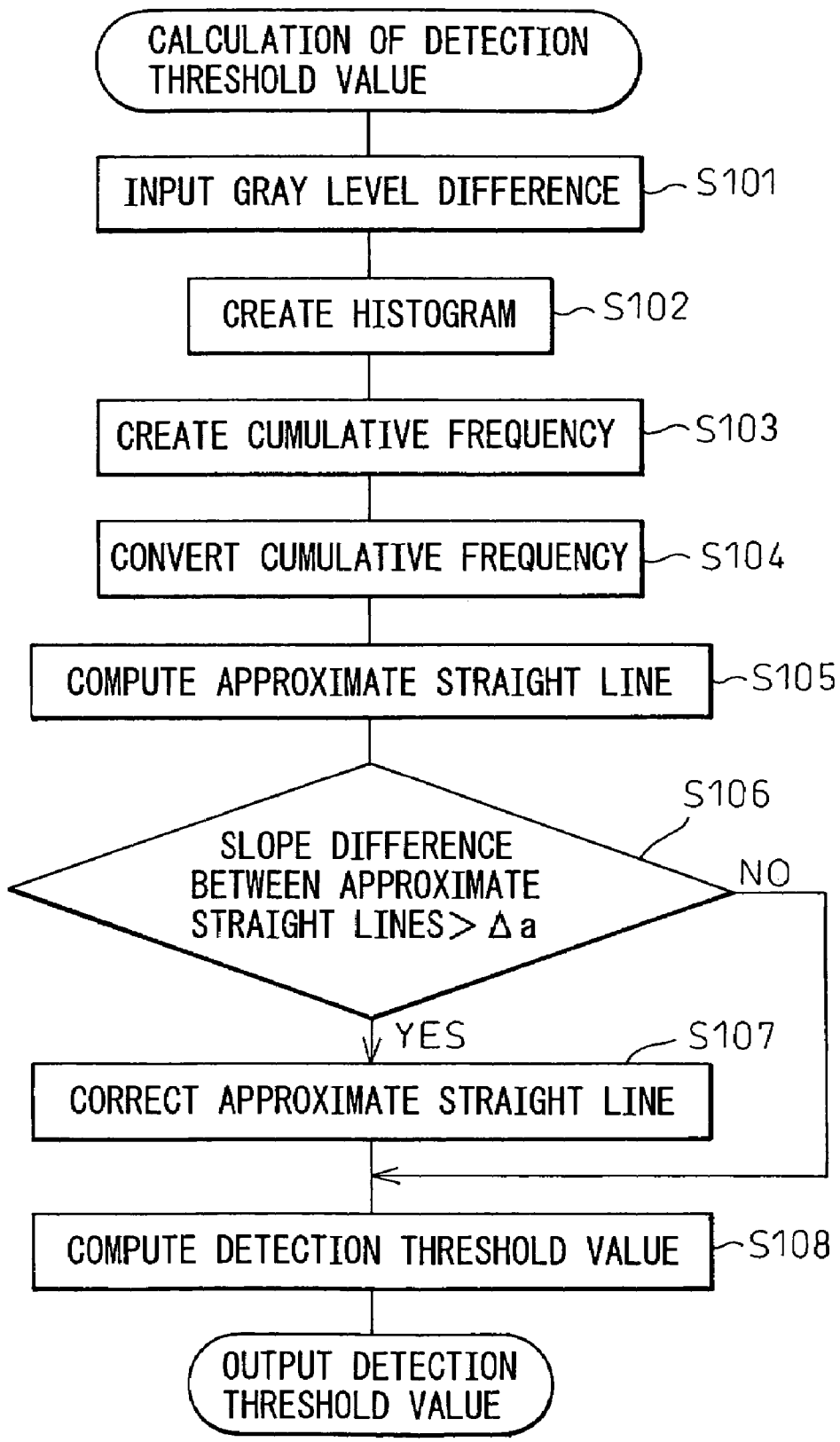
FIG. 6 is a flowchart illustrating the process for determining the detection threshold value according to the first embodiment.

FIG. 6 is a flowchart illustrating the detection threshold value calculation process performed in the detection threshold value calculation section 7. For examples of the graphs to be created in the process shown in the flowchart, reference should be made to the previously given FIGS. 1A to 1C.

Figure 1A:
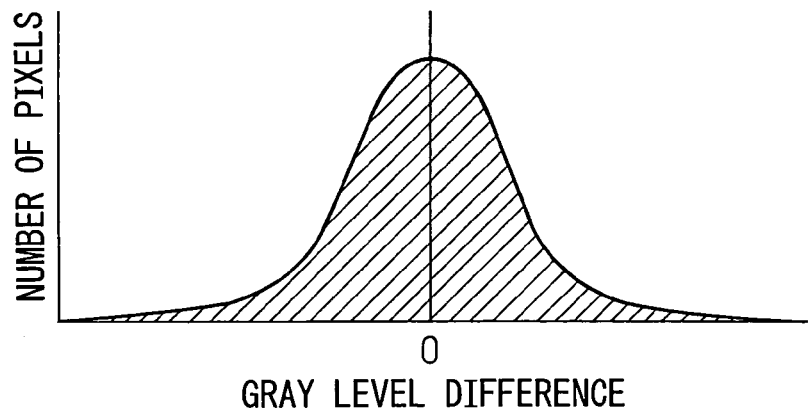
FIGS. 1A to 1C are diagrams for explaining a prior art image defect inspection method.
Figure 1B:
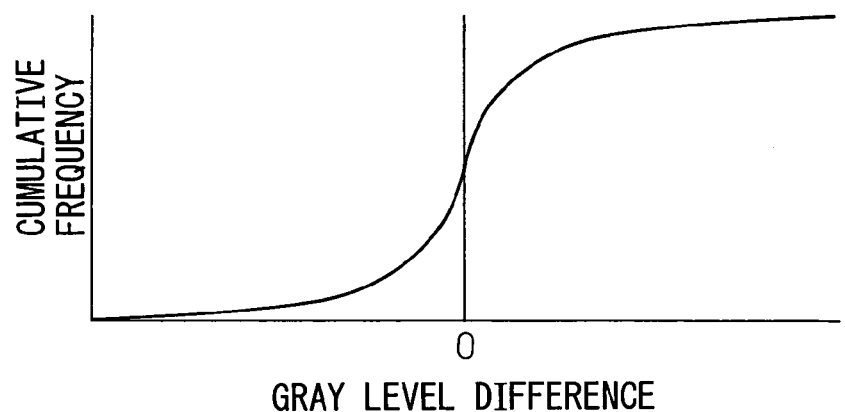
Figure 1C:
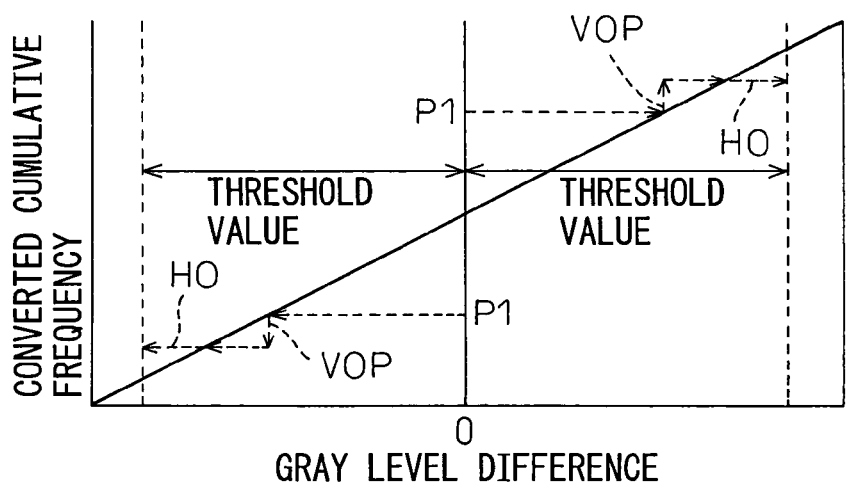
Figure 2A:
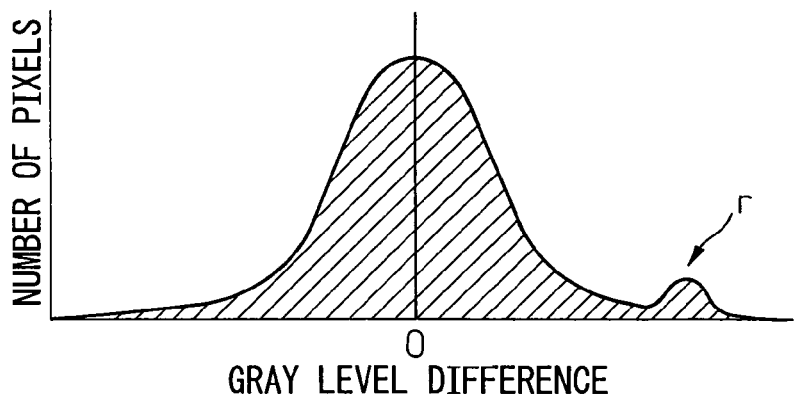
FIGS. 2A to 2D are diagrams for explaining the effect that a variation in a gray level difference distribution will have on a detection threshold value.
Figure 2B:
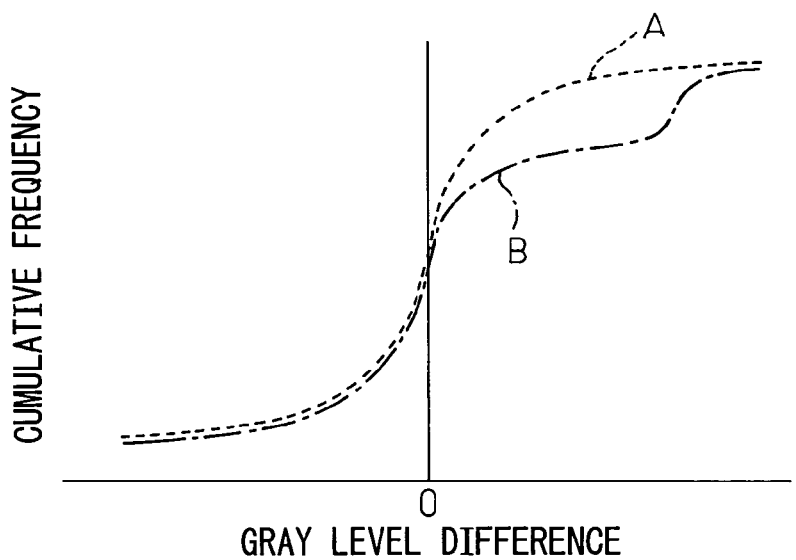
Figure 2C:
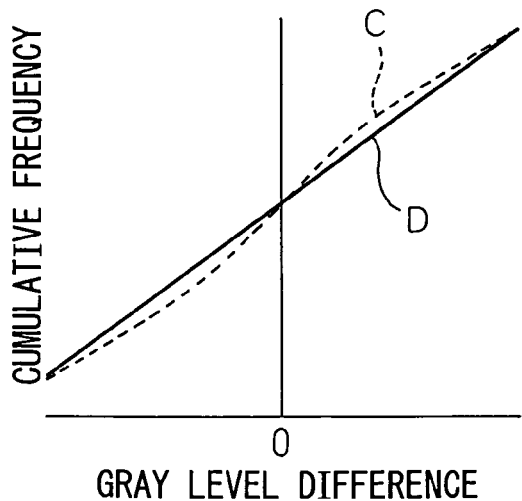
Figure 2D:
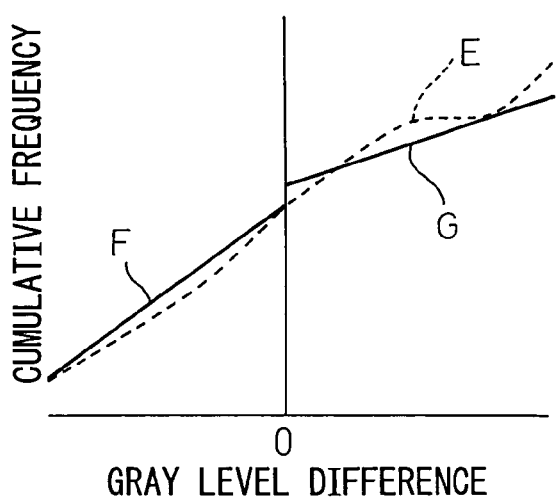

In step S101, the gray level difference, calculated pixel by pixel by the difference detection section 6, is input to the cumulative frequency computing section 11. In step S102, the cumulative frequency computing section 11 creates a histogram of gray level differences such as shown in FIG. 1A. Here, if the number of pixels to be inspected is large, the histogram need not necessarily be created by using the gray level differences of all the pixels, but may be created by using the gray level differences only of selectively sampled pixels.

In step S103, the cumulative frequency computing section 11 creates the cumulative frequency of the gray level difference based on the histogram. Here, instead of the cumulative frequency, cumulative probability may be created, as will be described later. The cumulative frequency computing section 11 supplies the thus created cumulative frequency to the conversion section 12.

Figure 7A:
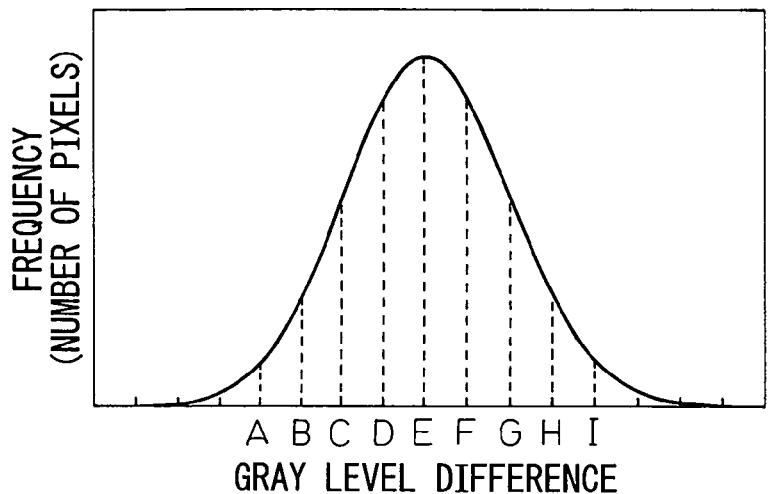
FIGS. 7A to 7C are diagrams for explaining the process for computing converted cumulative frequency.
Figure 7B:
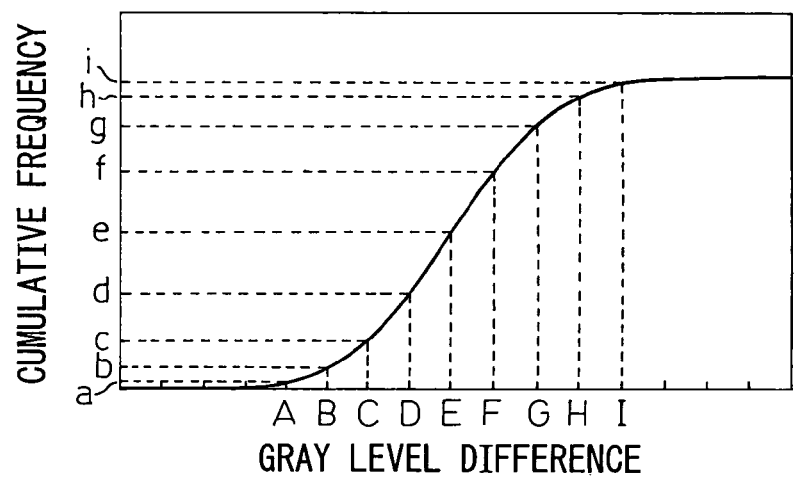

In step S104, assuming that the gray level difference obeys a certain type of distribution such as a normal distribution, a Poisson distribution, or a chi-squared distribution, the conversion section 12 converts the cumulative frequency so that the cumulative frequency shows a linear relationship to the gray level difference in the assumed distribution. It is assumed that the frequency of the gray level difference has a certain distribution such as shown in FIG. 7A. Then, its cumulative frequency is a monotonically increasing curve such as shown in FIG. 7B. If the curve is represented by probabilities by dividing each cumulative frequency by the total number of samples, curves having the same coefficient, which shows how widespread the distribution is, are identical. Next, the cumulative frequency is converted so that the cumulative frequency shows a linear relationship to the gray level difference. To describe more specifically, if values "a" to "i" in FIG. 7B are converted so that they are proportional to values A to I, the graph shown in FIG. 7C results; here, if the values A to I are equally spaced apart, then the values "a" to "i" are also equally spaced apart. The cumulative frequency thus converted will be called the converted cumulative frequency. To describe this process more specifically, if the probability of the gray level difference is denoted by f(t), the cumulative probability F(t) (cumulative frequency/number of samples) is expressed by the following equation 1.

$$F(t) = \int_{-\infty}^{t} f(x)dx \qquad (1)$$

Figure 7C:
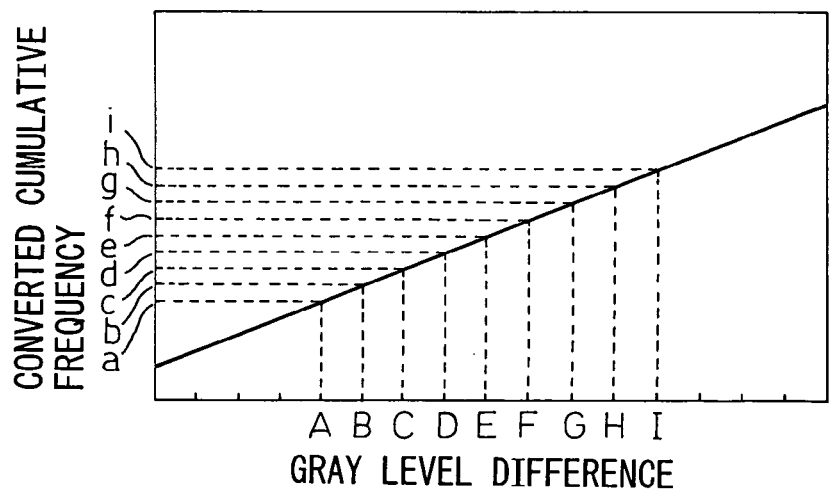

The conversion is accomplished by converting the cumulative probability by using the inverse function $F^{-1}(t)$ of the cumulative probability F(t). The converted cumulative frequency thus obtained is represented by a graph close to a straight line, such as shown in FIG. 7C. In the figure, the graph is shown in terms of cumulative frequency, but the graph is the same if it is shown in terms of cumulative probability. The converted cumulative frequency thus obtained is supplied to the approximate straight line computing section 13 at the subsequent stage.

As the computation for obtaining the inverse function of the cumulative probability requires a large amount of computation, the conversion is performed using a conversion table constructed in advance in accordance with the distribution. Further, the conversion need not be performed on all the cumulative frequency points, but need only be performed on the points necessary to obtain the approximate straight line hereinafter described. The assumed distribution can be created in advance by using a reference sample or a portion of the sample. As for the method of creating the assumed distribution from the reference, a histogram of gray level differences is created covering a region sufficiently larger than the range used to obtain the threshold value in the inspection. At this time, dies free from imperfections such as color unevenness or an area containing such dies are selected, or the average value of the signed gray level differences is obtained and a correction is made so that the gray level difference becomes zero at the average value, or a correction is made so that the gray level difference becomes zero when the probability is 50%. Then, the conversion table is constructed by obtaining the cumulative probability for each of the equally spaced gray level differences.

In step S105, the approximate straight line computing section 13 computes the approximate straight line (y=ax+b) from the relationship between the gray level difference and the converted cumulative frequency. Here, the approximate straight line computing section 13 computes approximate straight lines ($y=a_{(+)}x+b_{(+)}$ and $y=a_{(-)}x+b_{(-)}$) in the positive and negative gray level difference regions, respectively.

The approximate straight lines can be obtained using a least squares method or the like but, more simply, the approximate straight lines can each be obtained by joining a certain point on the converted cumulative frequency to the origin by a straight line. Each computed approximate straight line is supplied to the approximate straight line correction section 14 and the threshold value determining section 15.

In step S106, the approximate straight line correction section 14 compares the slopes ($a_{(+)}$ and $a_{(-)}$) of the two approximate straight lines input thereto. Then, if the difference between the slopes of the two approximate straight lines is larger than the predetermined value, of the approximate straight lines the approximate straight line having the smaller slope is corrected in step S107 in such a manner that its slope increases.

Figure 8A:
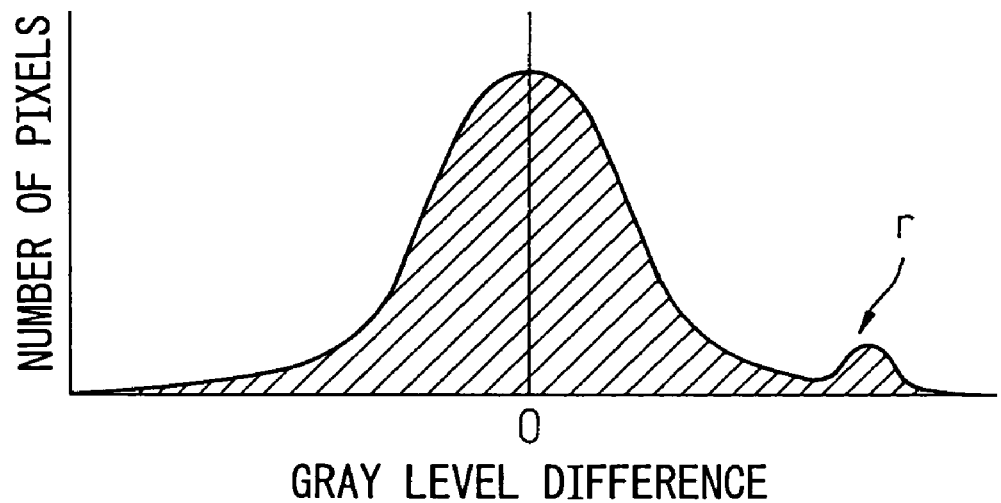
FIGS. 8A and 8B are diagrams for explaining the process for correcting the approximate straight line of the converted cumulative frequency.

Here, if there is a giant defect in the image of the die captured by the imaging device 4, the pixel gray level differences input to the cumulative frequency computing section 11 show a distribution (histogram) having a portion "r" corresponding to the defect, for example, as shown in FIG. 8A. In the example of FIG. 8A, the portion "r" corresponding to the giant defect occurs in the positive gray level difference region.

Figure 8B:
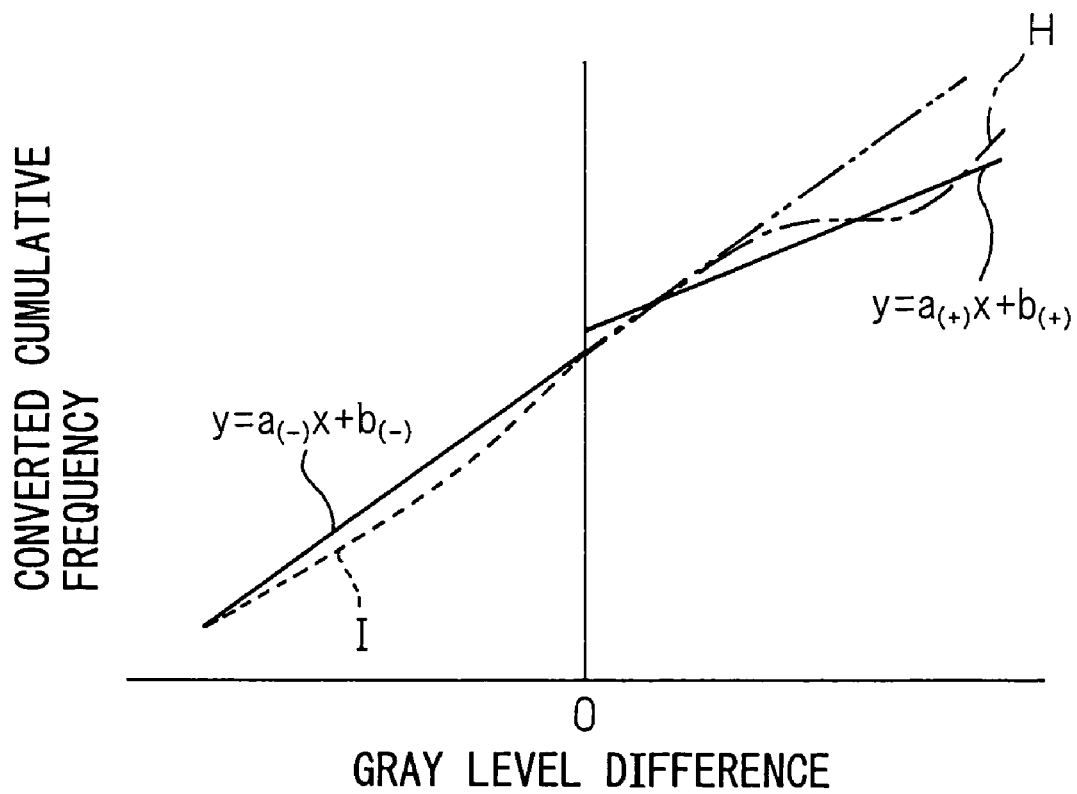

When a gray level difference associated with a defect is contained in the gray level differences to be processed, as described above, the converted cumulative frequency is approximated by a straight line up to the point of a certain gray level difference but, in the larger gray level difference region beyond that point, the straight line is shifted in a step-like manner, resulting in a discontinuous graph, as shown by a semi-dashed line H in FIG. 8B.

In this case, when the approximate straight line of the converted cumulative frequency is computed in each of the positive and negative gray level difference regions, the slope of the approximate straight line in the positive region ($y=a_{(+)}+b_{(+)}$) is smaller than the slope of the approximate straight line in the negative region ($y=a_{(-)}+b_{(-)}$). Therefore, when the difference between the slopes of the two approximate straight lines is larger than the predetermined value, the approximate straight line correction section 14 corrects the approximate straight line having the smaller slope (in the illustrated example, the approximate straight line in the positive region ($y=a_{(+)}+b_{(+)}$)) so as to increase its slope.

Here, the approximate straight line correction section 14 may increase the slope by adding a prescribed amount to the slope of the approximate straight line having the smaller slope, or may apply the correction in such a manner that the slope of the approximate straight line having the smaller slope becomes equal to that of the other approximate straight line. Alternatively, the correction may be made so that the slope becomes equal to the average of the slopes of the two approximate straight lines.

Further alternatively, the approximate straight line correction section 14 may correct the slope ($a_{(+)}$) of the approximate straight line having the smaller slope and, at the same time, obtain a corrected intercept by applying a correction to the intercept ($b_{(+)}$) at the Y axis (converted cumulative frequency axis), for example, by increasing or reducing the intercept ($b_{(+)}$) of the original approximate straight line by a prescribed amount or by making the intercept equal to the intercept ($b_{(-)}$) of the other approximate straight line.

In step S108, the threshold value is determined by using the parameters ($a_{(+)}$ and $b_{(+)}$, or $a_{(-)}$ and $b_{(-)}$) of the approximate straight line corrected in step S107, if it is determined in step S106 that the difference between the slopes of the two approximate straight lines is larger than the predetermined value; on the other hand, if it is determined that the difference between the slopes of the two approximate straight lines is equal to or less than the predetermined value, the threshold value is determined by using the parameters of the approximate straight line computed in step S105.

Figure 9:
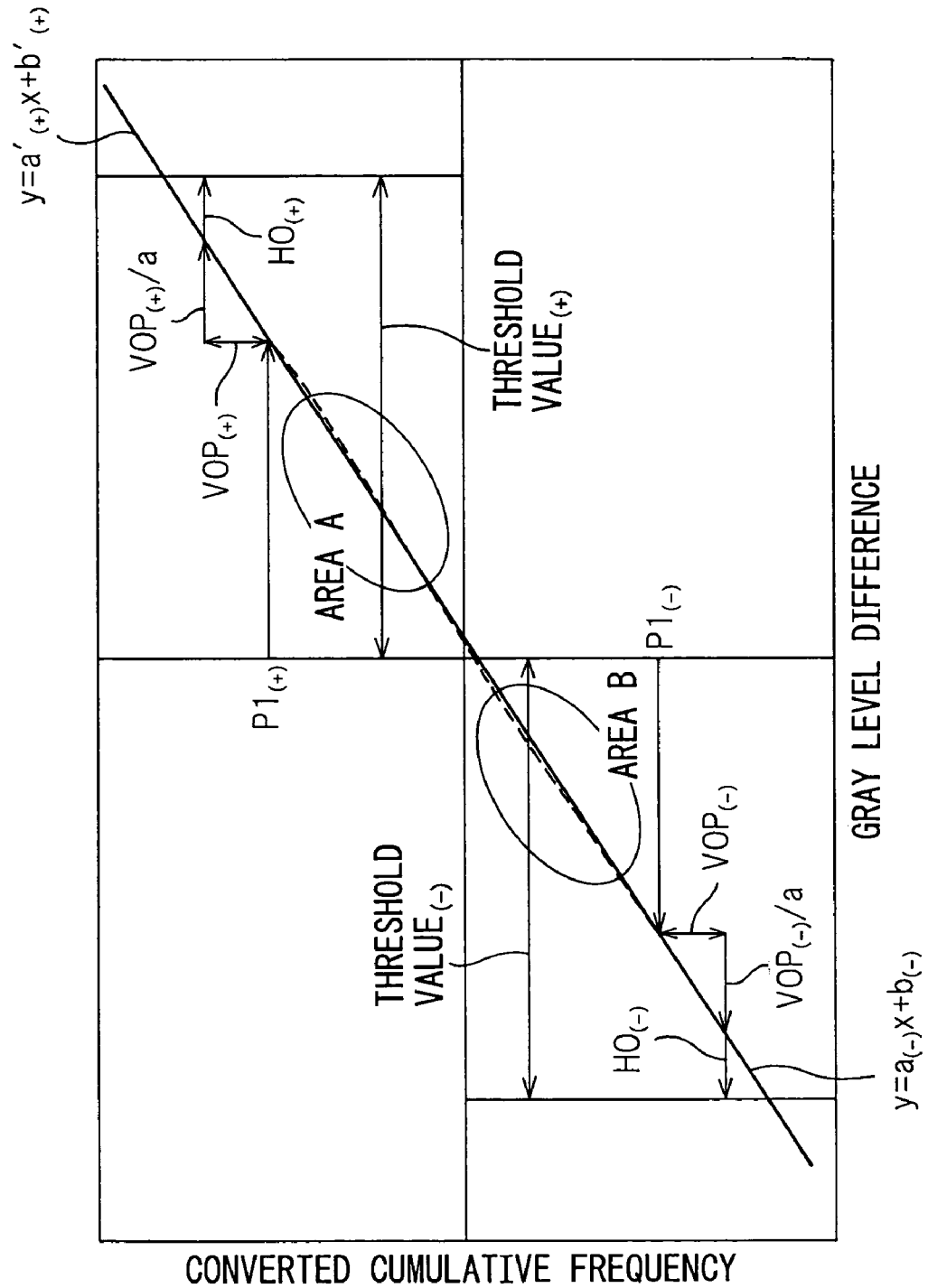
FIG. 9 is a diagram for explaining a first example of the process for determining the threshold value by using a graph showing the relationship between the gray level difference and the converted cumulative frequency.

FIG. 9 is a diagram for explaining a method of determining the threshold value. When using positive- or negative-signed gray level differences in the image defect inspection, both the positive threshold value $T_{(+)}$ and the negative threshold value $T_{(-)}$ are determined.

First, for the positive gray level region, $VOP_{(+)}$ and $HO_{(+)}$ are set as fixed sensitivity setting parameters, and the point on the straight line is obtained that represents the cumulative frequency $P1_{(+)}$ corresponding to the cumulative probability (p) ($P1_{(+)}$ is obtained by multiplying p by the number of samples); then, the gray level difference obtained by moving that point by $VOP_{(+)}$ in the vertical axis direction and by $HO_{(+)}$ in the horizontal axis direction is taken as the threshold value. Accordingly, the threshold value $T_{(+)}$ is expressed as $T_{(+)}=(P1_{(+)}-b_{(+)}+VOP_{(+)})/a_{(+)}+HO_{(+)}$.

Likewise, for the negative gray level region, $VOP_{(-)}$ and $HO_{(-)}$ are set as fixed sensitivity setting parameters, and the point on the straight line is obtained that represents the cumulative frequency $P1_{(-)}$ corresponding to the cumulative probability (p) ($P1_{(-)}$ is obtained by multiplying p by the number of samples); then, the gray level difference obtained by moving that point by $VOP_{(-)}$ in the vertical axis direction and by $HO_{(-)}$ in the horizontal axis direction is taken as the threshold value. Accordingly, the threshold value $T_{(-)}$ is expressed as $T_{(-)}=(P1_{(-)}-b_{(-)}+VOP_{(-)})/a_{(-)}+HO_{(-)}$.

In the threshold value determining method shown in FIG. 9, as can be seen from the above threshold value calculation equations, the threshold value $T_{(+)}$ is set smaller (the threshold value $T_{(-)}$ is set larger) as the slope of the approximate straight line becomes larger, and the threshold value $T_{(+)}$ is set larger (the threshold value $T_{(-)}$ is set smaller) as the slope "a" becomes smaller.

Accordingly, when the slope "a" is calculated to be smaller due to the effect of a giant defect, then in steps S106 and S107 a correction is applied so as to increase the slope "a" and, using this corrected slope "a", the threshold values are determined; this serves to prevent the range defined by the positive and negative threshold values from being set inappropriately wide.

Figure 10:
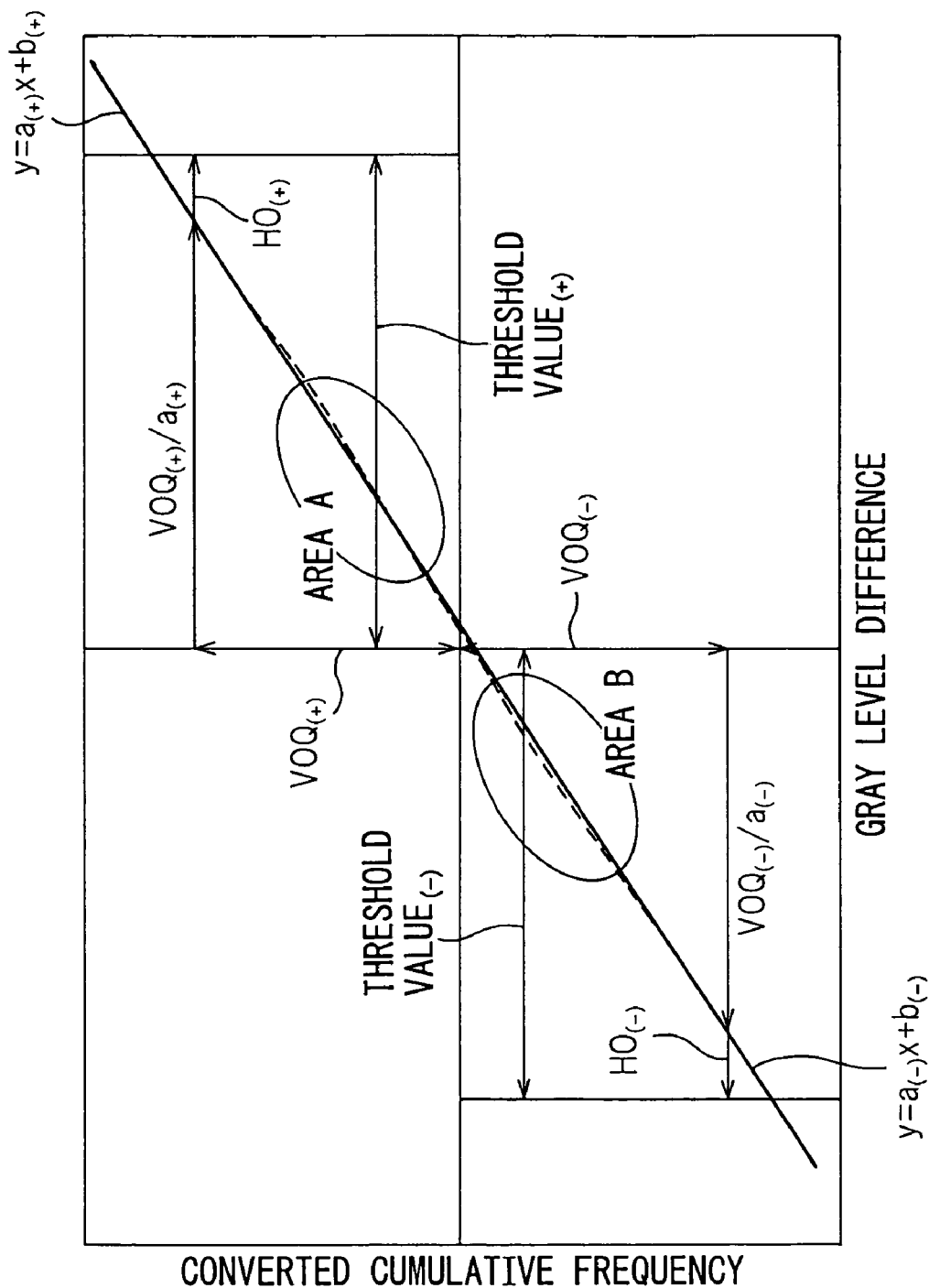
FIG. 10 is a diagram for explaining a second example of the process for determining the threshold value by using a graph showing the relationship between the gray level difference and the converted cumulative frequency.

As shown in FIG. 10, if $P1_{(+)}+VOP_{(+)}$ is set as $VOQ_{(+)}$ and $P1_{(-)}+VOP_{(-)}$ as $VOQ_{(-)}$, and $T_{(+)}=(VOQ_{(+)}-b_{(+)})/a_{(+)}+HO_{(+)}$ and $T_{(-)}=(VOQ_{(-)}-b_{(-)})/a_{(-)}+HO_{(-)}$ are calculated, the same results can be obtained.

After the positive threshold value $T_{(+)}$ and the negative threshold value $T_{(-)}$ have been determined, the detection section 8 determines whether there exist any defects in the captured image pattern of the die by checking whether the gray level difference AGL of each pixel lies within the range defined by the thus determined threshold values $T_{(+)}$ and $T_{(-)}$.

As described above, in the image defect inspection method and apparatus according to the first embodiment of the present invention, the detection threshold value is corrected by utilizing the fact that the approximate straight line of the converted cumulative frequency changes when the distribution of the gray level difference is different from the assumed usual distribution. In such a case, the coefficient of correlation between the converted cumulative frequency and the gray level difference decreases; therefore, the detection threshold value may be corrected by utilizing this correlation coefficient. An image defect inspection method and apparatus implementing this will be described with reference to FIGS. 11 to 14.

Figure 11:
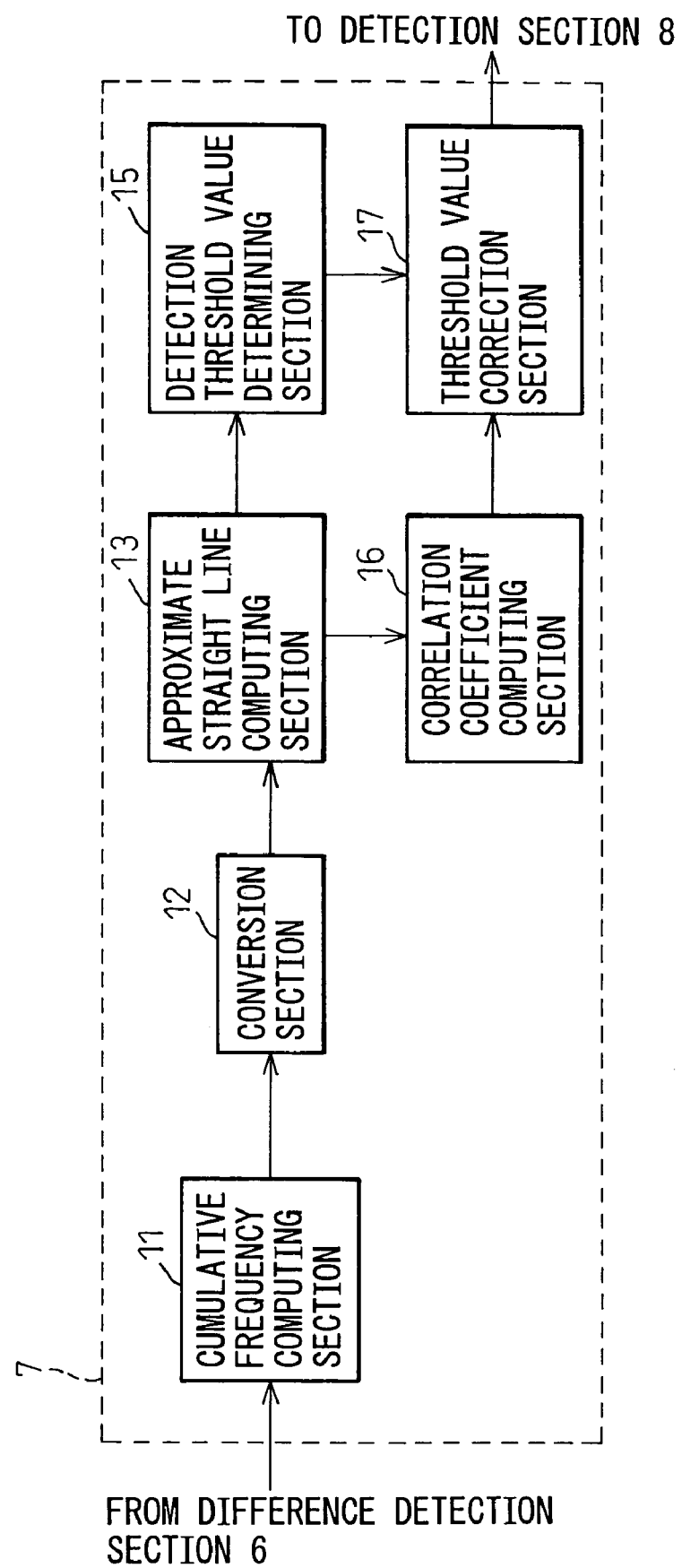
FIG. 11 is a block diagram showing the general configuration of a detection threshold value calculation section in an appearance inspection apparatus according to a second embodiment of the present invention.

FIG. 11 is a block diagram showing the general configuration of the detection threshold value calculation section 7 used in a semiconductor pattern appearance inspection apparatus according to a second embodiment of the present invention. The configuration of the appearance inspection apparatus itself is the same as that of the first embodiment shown in FIG. 3; therefore, the description of the component elements other than the detection threshold value calculation section 7 will not be repeated here.

As shown, the detection threshold value calculation section 7 comprises, in addition to the cumulative frequency computing section 11, the conversion section 12, the approximate straight line computing section 13 and the threshold value determining section 15 shown in the first embodiment, a correlation coefficient computing section 16 which computes the coefficient of correlation between the converted cumulative frequency computed by the conversion section 12 and the gray level difference, and a threshold value correction section 17 which corrects the threshold value determined by the threshold value determining section 15, in accordance with the correlation coefficient computed by the correlation coefficient computing section 16, and supplies the corrected threshold value to the detection section 8.

Figure 12:
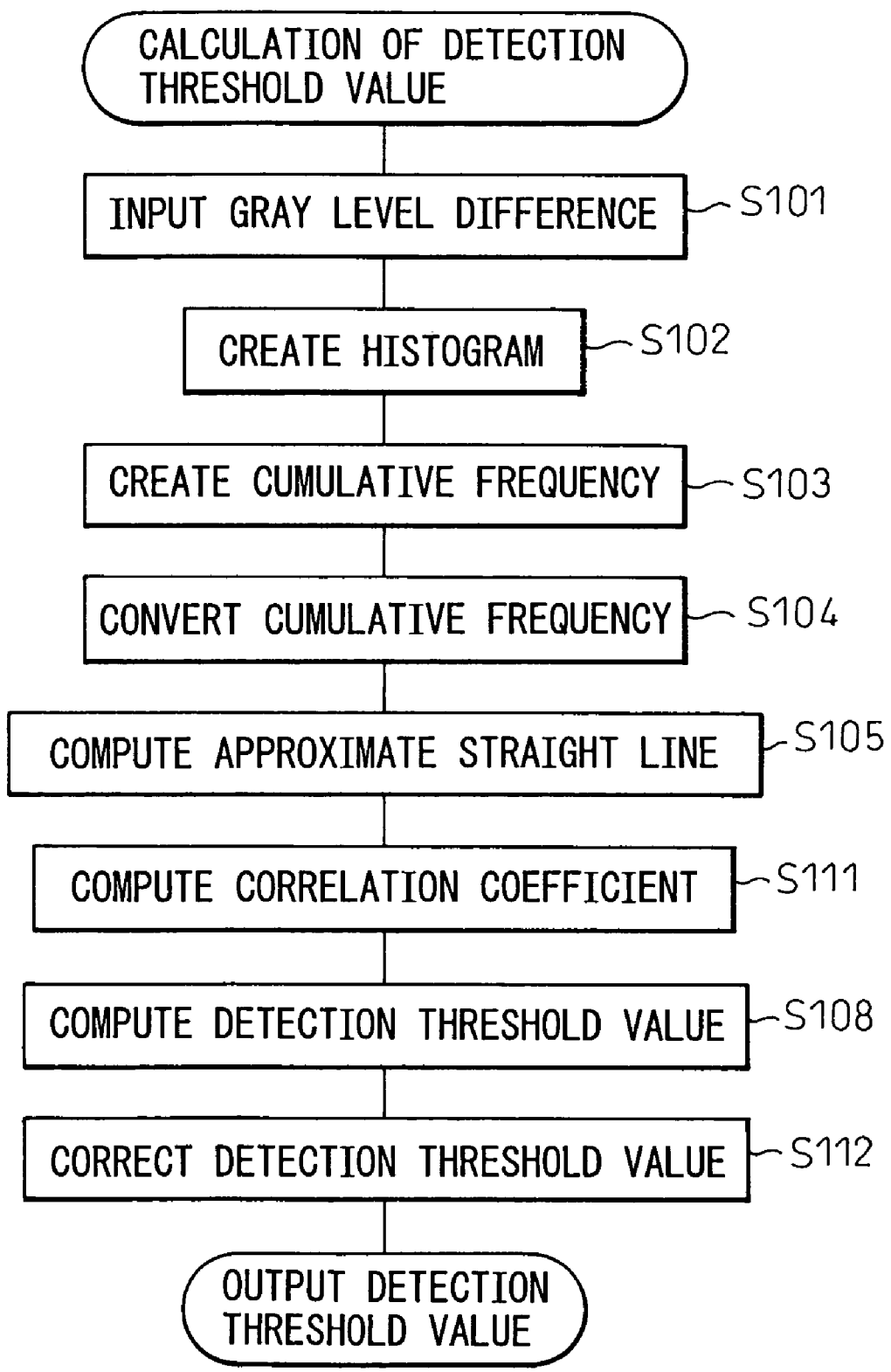
FIG. 12 is a flowchart illustrating the process for determining the detection threshold value according to the second embodiment.

The operation of the thus configured detection threshold value calculation section 7 and its component elements will be described with reference to FIGS. 12 to 14.

In steps S101 to S105, the approximate straight line of the converted cumulative frequency is computed from the input gray level difference data, as in the detection threshold value calculation section 7 of the first embodiment.

In step S111, for each sample value of the converted cumulative frequency that was used in step S105 to compute the approximate straight line using a least squares method or the like, the correlation coefficient computing section 16 computes the correlation coefficient r between the converted cumulative frequency and its corresponding gray level difference.

The correlation coefficient r can be obtained, for example, by the following equation.

$$\bar{x} = \sum_{i=1}^{n} \frac{x_i}{n}$$

$$\bar{y} = \sum_{i=1}^{n} \frac{y_i}{n}$$

$$r = \frac{\sum_{i=1}^{n}(x_i - \bar{x})(y_i - \bar{y})}{\sqrt{\sum_{i=1}^{n}(x_i - \bar{x})^2} \sqrt{\sum_{i=1}^{n}(y_i - \bar{y})^2}}$$ (2)

Here, xi (i is a natural number from 1 to n) indicates the gray level difference of each sample, yi the converted cumulative frequency of each sample, and n the number of samples.

Figure 13A:
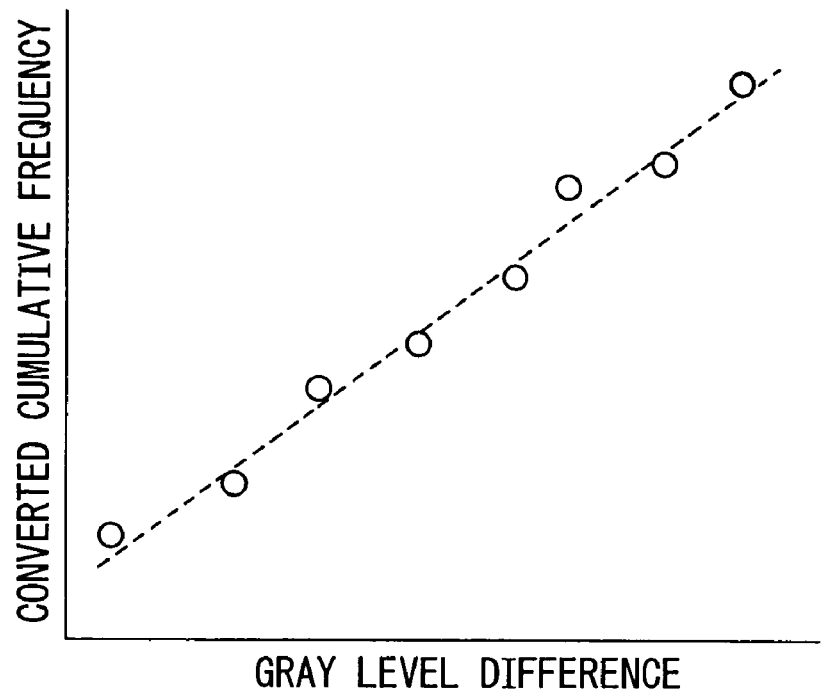
FIGS. 13A and 13B are diagrams for explaining a correlation efficient between the converted cumulative frequency and the gray level difference.
Figure 13B:
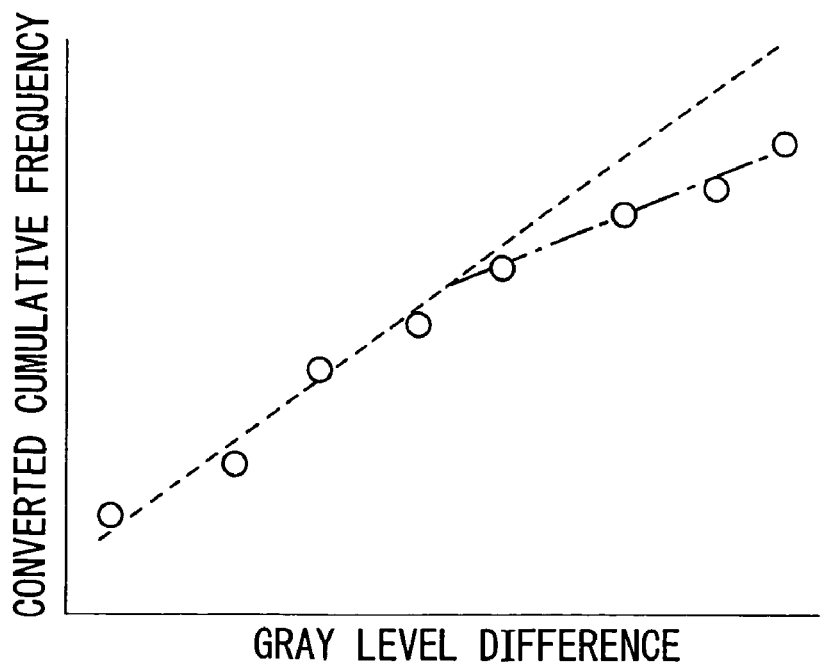

When the distribution of the gray level difference of the image under inspection is the usual distribution and is close to the distribution assumed in step S104, each sample value of the converted cumulative frequency is converted so as to provide a good linear approximation, as shown in FIG. 13A. Therefore, in this case, the correlation coefficient r increases (becomes closer to 1).

On the other hand, when the distribution of the gray level difference of the image under inspection greatly differs from the distribution assumed in step S104 because of such reasons as a large amount of noise contained in the image, each sample value is not converted linearly, as shown in FIG. 3B, and as a result, the correlation coefficient decreases.

Accordingly, after the threshold value has been determined by the threshold value determining section 15 in step S108, the threshold value correction section 17 corrects the determined threshold value in accordance with the correlation coefficient computed in step S111.

For example, the distribution assumed in step S104 is determined based on the assumption that the gray level difference of the image under inspection will exhibit a proper distribution. That is, the conversion section 12 determines the inverse function $F^{-1}(t)$ of the cumulative probability $F(t)$ of the gray level difference distribution obtained from an ideal or good reference sample, or constructs the conversion table based on such a distribution, and obtains the converted cumulative frequency by converting the cumulative frequency by using them.

Then, the threshold value correction section 17 corrects the threshold value determined by the threshold value determining section 15 in such a manner that the threshold value increases when the correlation coefficient r computed by the correlation coefficient computing section 16 decreases, that is, in such a manner that the threshold value becomes a decreasing function of the correlation coefficient r.

By correcting the threshold value in this manner, for the image under inspection whose correlation coefficient r is small (that is, in the case of an image containing much noise) the threshold value is increased and the detection sensitivity is reduced to prevent the occurrence of false defects, while for the image under inspection whose correlation coefficient r is large (that is, in the case of a good image having a proper distribution), the threshold value is held to a small value to maintain high detection sensitivity.

Figure 14A:
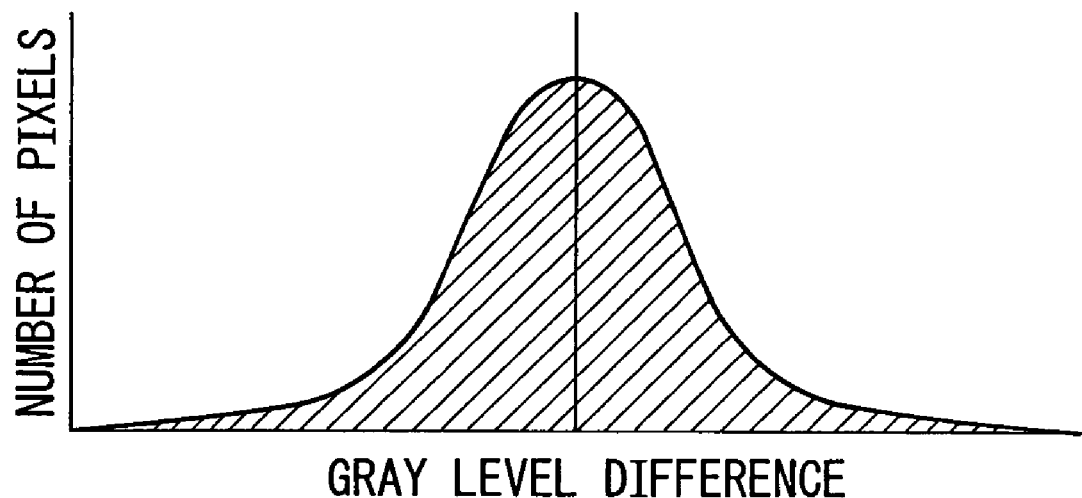
FIGS. 14A and 14B are diagrams each showing a prescribed distribution assumed in a conversion section.
Figure 14B:
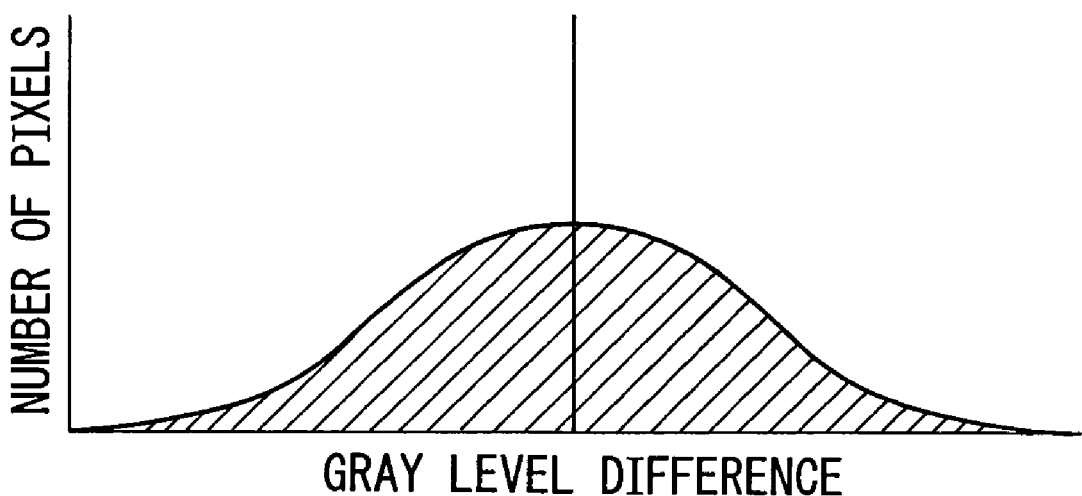

Alternatively, the assumed prescribed distribution used in step S104 may be determined based on the distribution of the gray level difference of a test image containing much noise (many defects). Such an assumed distribution may be given, for example, as shown in FIG. 14B. Compared with the usual distribution shown in FIG. 14A, the distribution shown in FIG. 14B is determined so as to have a somewhat wider distribution (sloping off gently) because of the prescribed amount of noise contained in the test image.

In this case, contrary to the case of the usual distribution, the threshold value correction section 17 corrects the threshold value determined by the threshold value determining section 15 in such a manner that the threshold value increases when the correlation coefficient r computed by the correlation coefficient computing section 16 increases, that is, in such a manner that the threshold value becomes an increasing function of the correlation coefficient r.

By correcting the threshold value in this manner, it also becomes possible to reduce the threshold value and increase the detection sensitivity when the image under inspection is one whose correlation coefficient r is small (that is, in the case of a good image containing little noise), while on the other hand, making it possible to increase the threshold value and reduce the detection sensitivity thereby preventing the occurrence of false defects when the image under inspection is one whose correlation coefficient r is large (that is, in the case of an image containing much noise).

As is apparent from the correction method of the threshold value correction section 17 described above, the gray level difference to be input to the threshold value correction section 17 may be input as positive- or negative-signed data or as absolute value data.

When using the absolute value data as the gray level difference, the difference detection section 6 outputs data representing the absolute difference between the gray level signals of two adjacent dies, and the detection section 8 compares this absolute difference data with the single threshold value determined by the threshold value calculation section 7. Here, the difference detection section 6 may be configured to obtain the absolute value data after correcting the signed data by subtracting from individual data such as the average value of the positive- or negative-signed gray level difference data, etc.

Figure 15:
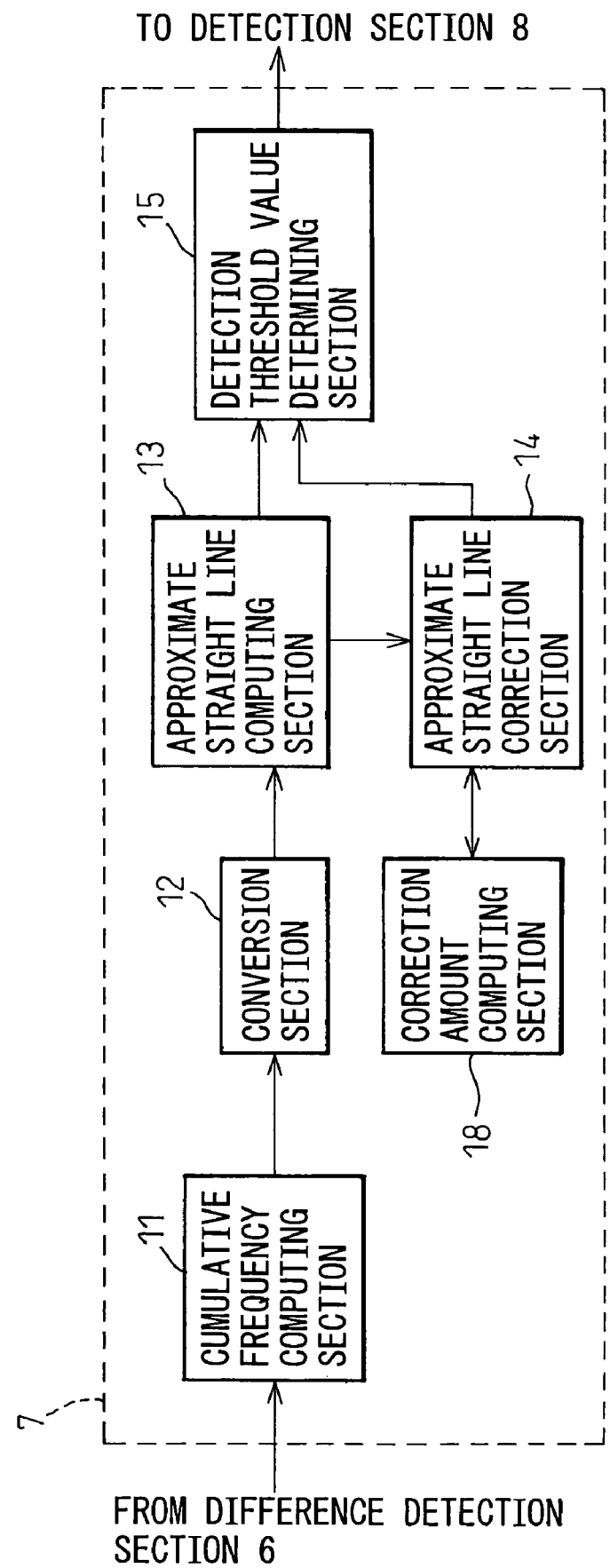
FIG. 15 is a block diagram showing the general configuration of a detection threshold value calculation section in an appearance inspection apparatus according to a third embodiment of the present invention.

FIG. 15 is a block diagram showing the general configuration of the detection threshold value calculation section 7 used in a semiconductor pattern appearance inspection apparatus according to a third embodiment of the present invention. The configuration of the appearance inspection apparatus itself is the same as that of the first embodiment shown in FIG. 3; therefore, the description of the component elements other than the detection threshold value calculation section 7 will not be repeated here.

As shown, the detection threshold value calculation section 7 comprises the cumulative frequency computing section 11, the conversion section 12, the approximate straight line computing section 13, the approximate straight line correction section 14, and the threshold value determining section 15, as in the first embodiment. In the present embodiment, the approximate straight line correction section 14 corrects the slope of each approximate straight line computed by the approximate straight line computing section 13, in accordance with the difference between the slopes of the respective approximate straight lines. For this purpose, the detection threshold value calculation section 7 further comprises a correction amount computing section 18 for computing the amount of correction by which to correct the slope of each approximate straight line.

The operation of the thus configured detection threshold value calculation section 7 and its component elements will be described with reference to FIGS. 16 and 17.

Figure 16:
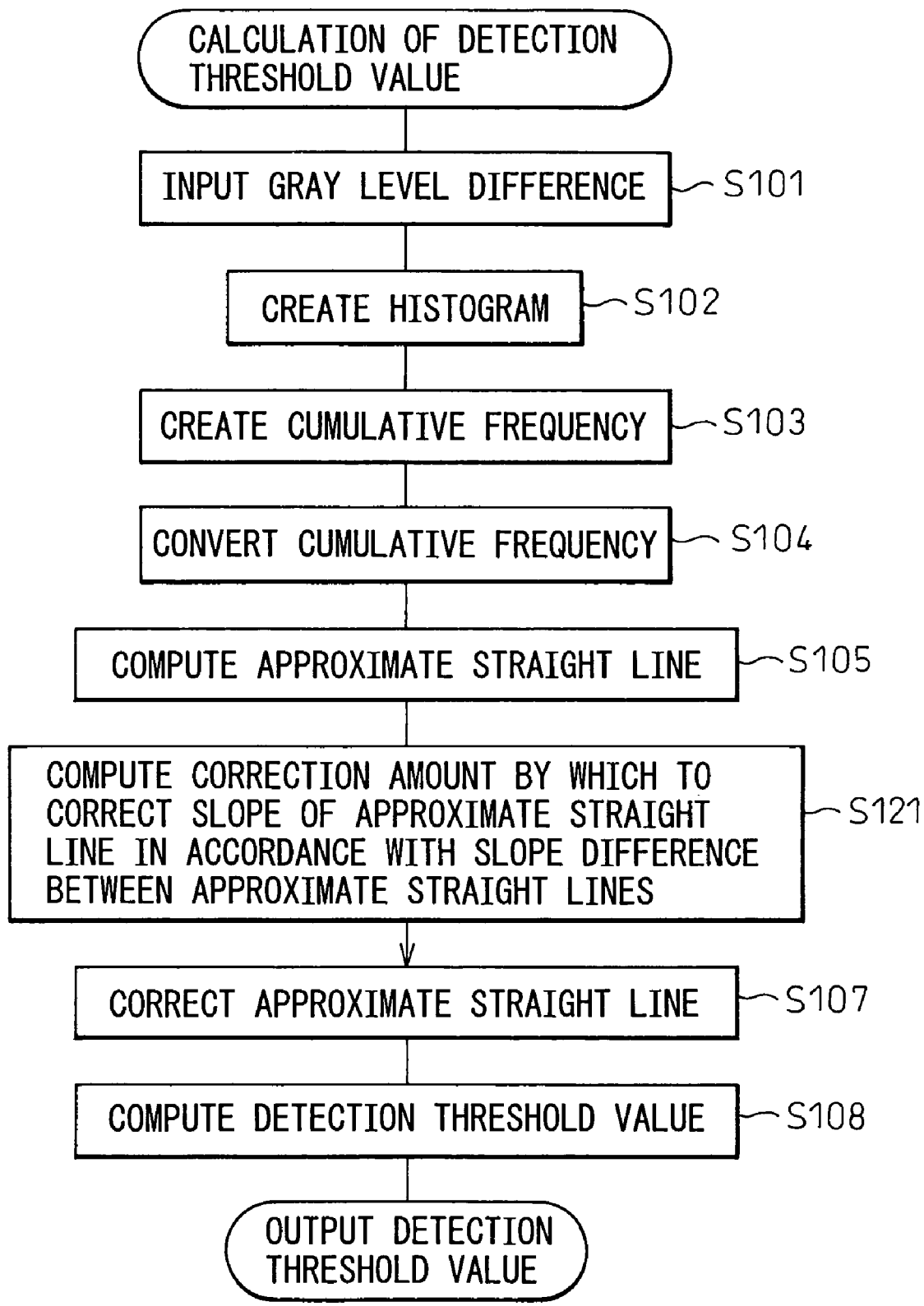
FIG. 16 is a flowchart illustrating the process for determining the detection threshold value according to the third embodiment.

FIG. 16 is a flowchart for determining the detection threshold value according to the present embodiment, and FIG. 17 is a diagram for explaining how the approximate straight line of the converted cumulative frequency is corrected according to the present embodiment.

Figure 17A:
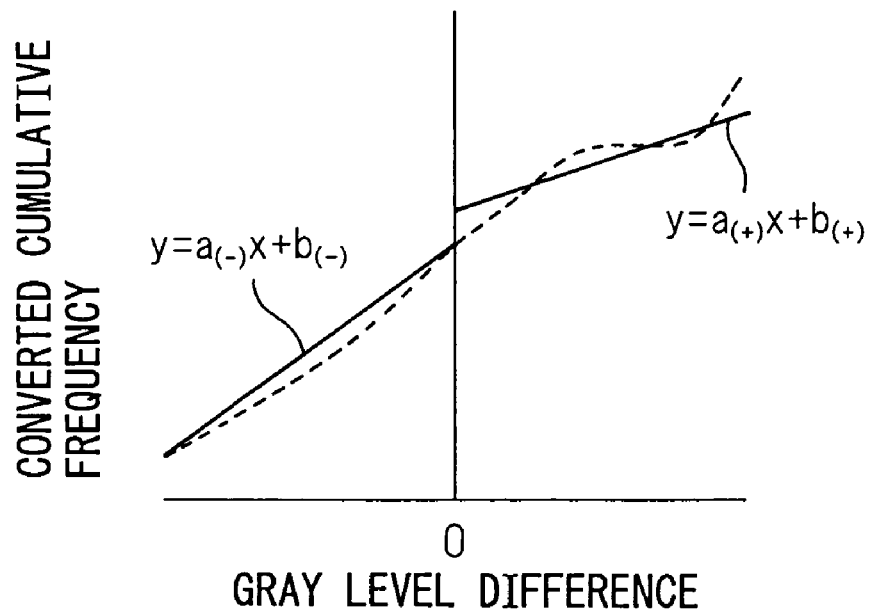
FIGS. 17A and 17B are diagrams for explaining the process for correcting the approximate straight line of the converted cumulative frequency according to the third embodiment.

In steps S101 to S105, the approximate straight line of the converted cumulative frequency is computed from the input gray level difference data, as in the detection threshold value calculation section 7 of the first embodiment. FIG. 17A shows the approximate straight lines $y=a_{(+)}x+b_{(+)}$ and $y=a_{(-)}x+b_{(-)}$ computed in the positive and negative gray level difference regions, respectively.

In step S121, the approximate straight line correction section 14 computes the difference $|a_{(+)}-a_{(-)}|$ between the slopes of the approximate straight lines $y=a_{(+)}x+b_{(+)}$ and $y=a_{(-)}x+b_{(-)}$. Then, the correction amount computing section 18 computes the amount of correction by which to correct the slope of each approximate straight line ($y=a_{(+)}x+b_{(+)}$, $y=a_{(-)}x+b_{(-)}$), in accordance with the slope difference $|a_{(+)}-a_{(-)}|$ computed by the approximate straight line correction section 14.

Figure 17B:
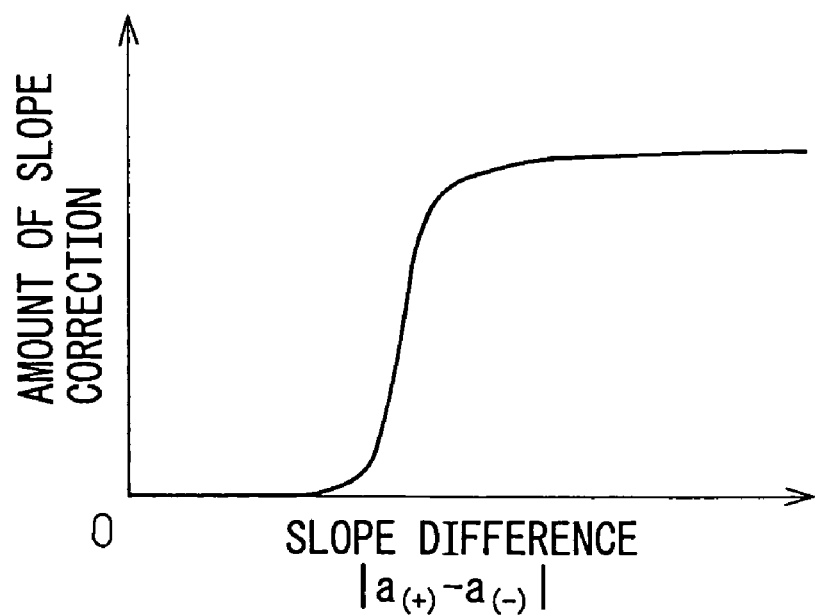

Here, the correction amount computing section 18 computes the amount of correction based, for example, on the predetermined relationship between the slope difference and its corresponding slope correction amount, such as shown by the graph of FIG. 17B, in such a manner that the amount of correction increases to increase the slope of the approximate straight line as the slope difference computed by the approximate straight line correction section 14 increases.

For this purpose, the correction amount computing section 18 may include such means as a means for calculating a function predetermined to indicate the relationship between the slope difference and its corresponding slope correction amount, and a lookup table prestored and used to search for the correction amount corresponding to the slope difference.

In step S107, the approximate straight line correction section 14 corrects the slope of the approximate straight line by the correction amount thus computed. At this time, the approximate straight line correction section 14 may compare the slopes of the approximate straight lines $y=a_{(+)}x+b_{(+)}$ and $y=a_{(-)}x+b_{(-)}$ computed in the positive and negative regions, respectively, and may correct (increase) the slope only of the approximate straight line having the smaller slope or may correct both the slope of the approximate straight line having the smaller slope and the slope of the approximate straight line having the larger slope.

When the approximate straight line correction section 14 is configured to correct both the slope of the approximate straight line having the smaller slope and the slope of the approximate straight line having the larger slope, the correction amount to be applied to one slope may be made different from the correction amount to be applied to the other. For example, the approximate straight line correction section 14 may correct the slope of the approximate straight line having the smaller slope by using the correction amount computed by the correction amount computing section 18 and correct the slope of the approximate straight line having the larger slope by an amount equal to a prescribed fraction of the amount computed by the correction amount computing section 18. Alternatively, the correction amount computing section 18 may be configured to compute separate correction amounts for the approximate straight line having the smaller slope and the approximate straight line having the larger slope, respectively, and the approximate straight line correction section 14 may correct the slopes of the respective approximate straight lines by using the respectively computed correction amounts.

Then, in step S108, the threshold value determining section 15 determines the threshold value by using the parameters ($a_{(+)}$ and $b_{(+)}$, or $a_{(-)}$ and $b_{(-)}$) of the approximate straight line whose slope has been corrected.

According to the present invention, even when there is a giant defect in the pattern under inspection, the detection threshold value can be automatically set by correcting for the effect of such a defect; this serves to prevent the detection threshold value from becoming excessively large, and thus the defect inspection can be performed by maintaining high detection sensitivity.

Further, by correcting the detection threshold value in accordance with the correlation coefficient, it becomes possible to automatically use a high detection sensitivity when the image under inspection contains little noise and low detection sensitivity when the image under inspection contains much noise; accordingly, the defect inspection can be performed by maintaining high sensitivity while suppressing the occurrence of false defects.

The present invention is applicable to an image defect inspection method and apparatus in which two corresponding images under inspection are compared and, if the difference is large, either one of them is judged to be defective; in particular, the invention is applicable to an appearance inspection apparatus for detecting a defect in a circuit pattern such as a semiconductor circuit pattern formed on a semiconductor wafer.

While the invention has been described with reference to specific embodiments chosen for purpose of illustration, it should be apparent that numerous modifications could be made thereto by those skilled in the art without departing from the basic concept and scope of the invention.

What is claimed is:

1. An image defect inspection method which detects a gray level difference between corresponding portions of two images, compares said detected gray level difference with a threshold value, and judges one or the other of said portions to be defective if said gray level difference is larger than said threshold value, wherein a cumulative frequency of said gray level difference between said two images is computed, a converted cumulative frequency is computed by converting said cumulative frequency so that said cumulative frequency shows a linear relationship to said gray level difference when said gray level difference is assumed to have a distribution that obeys a prescribed type of distribution, an approximate straight line is computed by approximating said converted cumulative frequency by a straight line in each of two regions, one where said gray level difference is positive and the other where said gray level difference is negative, when the difference between the slopes of said approximate straight lines is larger than a predetermined value, the approximate straight line having the smaller slope is corrected in such a manner said slope increases, based on said approximate straight line, said threshold value is determined from a prescribed cumulative frequency value in accordance with a prescribed calculation method, and said comparison is performed using said determined threshold value.

2. An image defect inspection method as claimed in claim 1, wherein when the difference between the slopes of said approximate straight lines is larger than said predetermined value, the approximate straight line having the smaller slope is corrected in such a manner said slope increases by a predetermined amount.

3. An image defect inspection method as claimed in claim 1, wherein when the difference between the slopes of said approximate straight lines is larger than said predetermined value, the approximate straight line having the smaller slope is corrected in such a manner said slope becomes equal to the slope of the other approximate straight line.

4. An image defect inspection method as claimed in claim 1, wherein when the difference between the slopes of said approximate straight lines is larger than said predetermined value, the approximate straight line having the smaller slope is corrected in such a manner said slope becomes equal to an average taken between the slopes of said approximate straight lines.

5. An image defect inspection method which detects a gray level difference between corresponding portions of two images, compares said detected gray level difference with a threshold value, and judges one or the other of said portions to be defective if said gray level difference is larger than said threshold value, wherein a cumulative frequency of said gray level difference between said two images is computed, a converted cumulative frequency is computed by converting said cumulative frequency so that said cumulative frequency shows a linear relationship to said gray level difference when said gray level difference is assumed to have a distribution that obeys a prescribed type of distribution, an approximate straight line is computed by approximating said converted cumulative frequency by a straight line, a correlation coefficient between said converted cumulative frequency and said gray level difference is computed, based on said approximate straight line, said threshold value is determined from a prescribed cumulative frequency value in accordance with a prescribed calculation method, said determined threshold value is corrected in accordance with said computed correlation coefficient, and said comparison is performed using said corrected threshold value.

6. An image defect inspection method as claimed in claim 5, wherein said determined threshold value is corrected in such a manner said threshold value increases as said computed correlation coefficient decreases.

7. An image defect inspection method as claimed in claim 5, wherein said prescribed type of distribution is determined by assuming the distribution that the gray level difference between two images containing a prescribed amount of noise will exhibit, and said determined threshold value is corrected in such a manner said threshold value increases as said computed correlation coefficient increases.

8. An image defect inspection method which detects a gray level difference between corresponding portions of two images, compares said detected gray level difference with a threshold value, and judges one or the other of said portions to be defective if said gray level difference is larger than said threshold value, wherein a cumulative frequency of said gray level difference between said two images is computed, a converted cumulative frequency is computed by converting said cumulative frequency so that said cumulative frequency shows a linear relationship to said gray level difference when said gray level difference is assumed to have a distribution that obeys a prescribed type of distribution, an approximate straight line is computed by approximating said converted cumulative frequency by a straight line in each of two regions, one where said gray level difference is positive and the other where said gray level difference is negative, at least one of said approximate straight lines is corrected in accordance with the difference between the slopes of said approximate straight lines, based on said approximate straight line, said threshold value is determined from a prescribed cumulative frequency value in accordance with a prescribed calculation method, and said comparison is performed using said determined threshold value.

9. An image defect inspection apparatus comprising:

a difference image detection section which detects a gray level difference between corresponding portions of two images;

a defect detection section which compares said detected gray level difference with a threshold value, and judges one or the other of said portions to be defective if said gray level difference is larger than said threshold value; and a detection threshold value calculation section which changes said threshold value in accordance with the distribution of said detected gray level difference, wherein said detection threshold value calculation section comprises:

a cumulative frequency computing section which computes a cumulative frequency of said gray level difference between said two images;

a conversion section which computes a converted cumulative frequency by converting said cumulative frequency so that said cumulative frequency shows a linear relationship to said gray level difference when said gray level difference is assumed to have a distribution that obeys a prescribed type of distribution;

an approximate straight line computing section which computes an approximate straight line by approximating said converted cumulative frequency by a straight line in each of two regions, one where said gray level difference is positive and the other where said gray level difference is negative;

an approximate straight line correction section which, when the difference between the slopes of said approximate straight lines is larger than a predetermined value, corrects the approximate straight line having the smaller slope in such a manner said slope increases; and a threshold value determining section which, based on said approximate straight line, determines said threshold value from a prescribed cumulative frequency value in accordance with a prescribed calculation method, wherein said comparison is performed using said determined threshold value.

10. An image defect inspection apparatus as claimed in claim 9, wherein when the difference between the slopes of said approximate straight lines is larger than said predetermined value, said approximate straight line correction section corrects the approximate straight line having the smaller slope in such a manner said slope increases by a predetermined amount.

11. An image defect inspection apparatus as claimed in claim 9, wherein when the difference between the slopes of said approximate straight lines is larger than said predetermined value, said approximate straight line correction section corrects the approximate straight line having the smaller slope in such a manner said slope becomes equal to the slope of the other approximate straight line.

12. An image defect inspection apparatus as claimed in claim 9, wherein when the difference between the slopes of said approximate straight lines is larger than said predetermined value, said approximate straight line correction section corrects the approximate straight line having the smaller slope in such a manner said slope becomes equal to an average taken between the slopes of said approximate straight lines.

13. An appearance inspection apparatus for detecting a defect in a semiconductor circuit pattern formed on a semiconductor wafer, comprising:

imaging means for generating an image of said semiconductor circuit pattern formed on said semiconductor wafer; and an image defect inspection apparatus as claimed in claim 9, wherein said image defect inspection apparatus detects a defect in said semiconductor circuit pattern.

14. An image defect inspection apparatus comprising:

a difference image detection section which detects a gray level difference between corresponding portions of two images;

a defect detection section which compares said detected gray level difference with a threshold value, and judges one or the other of said portions to be defective if said gray level difference is larger than said threshold value; and a detection threshold value calculation section which changes said threshold value in accordance with the distribution of said detected gray level difference, wherein said detection threshold value calculation section comprises:

a cumulative frequency computing section which computes a cumulative frequency of said gray level difference between said two images;

a conversion section which computes a converted cumulative frequency by converting said cumulative frequency so that said cumulative frequency shows a linear relationship to said gray level difference when said gray level difference is assumed to have a distribution that obeys a prescribed type of distribution;

an approximate straight line computing section which computes an approximate straight line by approximating said converted cumulative frequency by a straight line;

a correlation coefficient computing section which computes a correlation coefficient between said converted cumulative frequency and said gray level difference;

a threshold value determining section which, based on said approximate straight line, determines said threshold value from a prescribed cumulative frequency value in accordance with a prescribed calculation method; and a threshold value correction section which corrects said determined threshold value in accordance with said computed correlation coefficient, wherein said comparison is performed using said corrected threshold value.

15. An image defect inspection apparatus as claimed in claim 14, wherein said threshold value correction section corrects said determined threshold value in such a manner said threshold value increases as said computed correlation coefficient decreases.

16. An image defect inspection apparatus as claimed in claim 14, wherein said conversion section computes said converted cumulative frequency based on said prescribed type of distribution that is determined by assuming the distribution that the gray level difference between two images containing a prescribed amount of noise will exhibit, and said threshold value correction section corrects said determined threshold value in such a manner said threshold value increases as said computed correlation coefficient increases.

17. An appearance inspection apparatus for detecting a defect in a semiconductor circuit pattern formed on a semiconductor wafer, comprising:

imaging means for generating an image of said semiconductor circuit pattern formed on said semiconductor wafer; and an image defect inspection apparatus as claimed in claim 14, wherein said image defect inspection apparatus detects a defect in said semiconductor circuit pattern.

18. An image defect inspection apparatus comprising:

a difference image detection section which detects a gray level difference between corresponding portions of two images;

a defect detection section which compares said detected gray level difference with a threshold value, and judges one or the other of said portions to be defective if said gray level difference is larger than said threshold value; and a detection threshold value calculation section which changes said threshold value in accordance with the distribution of said detected gray level difference, wherein said detection threshold value calculation section comprises:

a cumulative frequency computing section which computes a cumulative frequency of said gray level difference between said two images;

a conversion section which computes a converted cumulative frequency by converting said cumulative frequency so that said cumulative frequency shows a linear relationship to said gray level difference when said gray level difference is assumed to have a distribution that obeys a prescribed type of distribution;

an approximate straight line computing section which computes an approximate straight line by approximating said converted cumulative frequency by a straight line in each of two regions, one where said gray level difference is positive and the other where said gray level difference is negative;

an approximate straight line correction section which corrects at least one of said approximate straight lines in accordance with the difference between the slopes of said approximate straight lines; and a threshold value determining section which, based on said approximate straight line, determines said threshold value from a prescribed cumulative frequency value in accordance with a prescribed calculation method, wherein said comparison is performed using said determined threshold value.

19. An appearance inspection apparatus for detecting a defect in a semiconductor circuit pattern formed on a semiconductor wafer, comprising:

imaging means for generating an image of said semiconductor circuit pattern formed on said semiconductor wafer; and an image defect inspection apparatus as claimed in claim 18, wherein said image defect inspection apparatus detects a defect in said semiconductor circuit pattern.

* * * * *